(12) United States Patent
Cho et al.

(10) Patent No.: US 10,564,816 B2
(45) Date of Patent: Feb. 18, 2020

(54) ELECTRONIC DEVICE FOR INPUTTING SLEEPING INFORMATION AND METHOD OF CONTROLLING THE SAME

(71) Applicant: Samsung Electronics Co., Ltd., Gyeonggi-do (KR)

(72) Inventors: Seong-Ho Cho, Seoul (KR); Eun-Joo Myung, Seoul (KR); Ah-Ram Suh, Seoul (KR); Seung-Won Lee, Gyeonggi-do (KR); Yoon-Ju Cho, Gyeonggi-do (KR)

(73) Assignee: Samsung Electronics Co., Ltd., Yeongtong-gu, Suwon-si, Gyeonggi-do (KR)

( * ) Notice: Subject to any disclaimer, the term of this patent is extended or adjusted under 35 U.S.C. 154(b) by 393 days.

(21) Appl. No.: 15/013,296

(22) Filed: Feb. 2, 2016

(65) Prior Publication Data

US 2016/0235359 A1    Aug. 18, 2016

(30) Foreign Application Priority Data

Feb. 12, 2015  (KR) ..................... 10-2015-0021880

(51) Int. Cl.
*A61B 5/0205*  (2006.01)
*G06F 3/0484*  (2013.01)

(52) U.S. Cl.
CPC ........ *G06F 3/0484* (2013.01); *A61B 5/02055* (2013.01)

(58) Field of Classification Search
CPC .......................................... A61B 5/4806–4815
See application file for complete search history.

(56) References Cited

U.S. PATENT DOCUMENTS

| | | | |
|---|---|---|---|
| 2003/0018242 A1* | 1/2003 | Hursh ....................... | A61B 5/16 600/300 |
| 2011/0144455 A1* | 6/2011 | Young .................. | A61B 5/0205 600/301 |
| 2012/0065893 A1* | 3/2012 | Lee ......................... | G06Q 10/10 702/19 |
| 2014/0122483 A1 | 5/2014 | Zhang et al. | |
| 2014/0222720 A1* | 8/2014 | Hames ................... | G16H 10/20 706/11 |
| 2015/0073289 A1* | 3/2015 | Lim ..................... | A61B 5/7282 600/529 |

* cited by examiner

*Primary Examiner* — George R Evanisko
(74) *Attorney, Agent, or Firm* — Cha & Reiter, LLC.

(57) ABSTRACT

A method comprising: displaying, by an electronic device, a sleep information input screen determined according to a prestored sleep pattern; detecting an input of sleep information to the sleep information input screen; and storing the sleep information in a memory of the electronic device.

13 Claims, 33 Drawing Sheets

| | | 561 | | 571 | | |
|---|---|---|---|---|---|---|
| | 550 | 560 | | 570 | 580 | |
| | DATE | BEDTIME | | WAKE-UP TIME | SLEEP TIME | |
| 551 | 1/29 | 12:40 AM | | 7:20 AM | 6h 40min | 581 |
| 552 | 1/30 | 12:41 AM | | 7:20 AM | 6h 39min | 582 |
| | | 562 | | 572 | | |

ELECTRONIC DEVICE FOR INPUTTING SLEEPING INFORMATION AND METHOD OF CONTROLLING THE SAME

CLAIM OF PRIORITY

This application claims the priority under 35 U.S.C. § 119(a) to Korean Application Serial No. 10-2015-0021880, which was filed in the Korean Intellectual Property Office on Feb. 12, 2015, the entire content of which is hereby incorporated by reference.

TECHNICAL FIELD

The present disclosure relates to electronic devices in general, and more particularly, to an electronic device for inputting sleeping information and method for controlling the same.

BACKGROUND

Recently, research on the utilization of a sleeping record has been actively researched. The sleeping record is one of the important indexes, based on which the health state of a user may be determined, and it is possible to determine the health state of the user and to suggest an life habits by utilizing the sleeping record. Accordingly, a manager, such as a doctor, determining the health state of the user may recognize a sleeping habit by asking the patient. A patient may provide a sleeping record by writing the sleeping record every day and providing the written sleeping record. However, the user has the burden of recording the sleeping time and wake-up time every day and it may be difficult to provide an accurate sleeping record.

In the meantime, mobile terminals providing wireless communication between users have been developed. According to the advancement of technology, wireless terminals provide many additional specifications in addition to a simple call communication. For example, mobile terminals provide additional functions, such as an alarm, a Short Messaging Service (SMS), a Multimedia Message Service (MMS), an E-mail, a game, a remote control of short range communication, an image capturing function using a mounted digital camera, a multimedia function for providing audio and video contents, a scheduling function, and other similar functions.

SUMMARY

As described above, a user may have the burden of recording the sleeping time and wake-up time every day and it may be difficult to provide an accurate sleeping record. Further, a mobile electronic device and a wearable electronic device, which secure portability, have been actively introduced, so that the development of a technology for a sleeping record using the mobile electronic device and a wearable electronic device has been requested.

The present disclosure is conceived to solve the aforementioned problems or other problems and to respond to the request of the technology development.

According to aspects of the disclosure, a method is provided comprising: displaying, by an electronic device, a sleep information input screen determined according to a prestored sleep pattern; detecting an input of sleep information to the sleep information input screen; and storing the sleep information in a memory of the electronic device.

According to aspects of the disclosure, an electronic device is provided, comprising: a display; a memory; and at least one processor operatively coupled to the memory, configured to: display a sleep information input screen determined according to a prestored sleep pattern on the display; detect an input of sleep information to the sleep information input screen; and store the sleep information in the memory.

According to aspects of the disclosure, a non-transitory computer-readable storage medium is provided that stores one or more processor-executable instructions, which when executed by at least one processor cause the at least one processor to perform a method comprising the steps of: displaying a sleep information input screen; detecting an input of sleep information to the sleep information input screen; and storing the sleep information in a memory that is operatively coupled to the processor.

BRIEF DESCRIPTION OF THE DRAWINGS

The above and other aspects, features, and advantages of the present disclosure will be more apparent from the following detailed description taken in conjunction with the accompanying drawings, in which.

DETAILED DESCRIPTION

Figure 1:
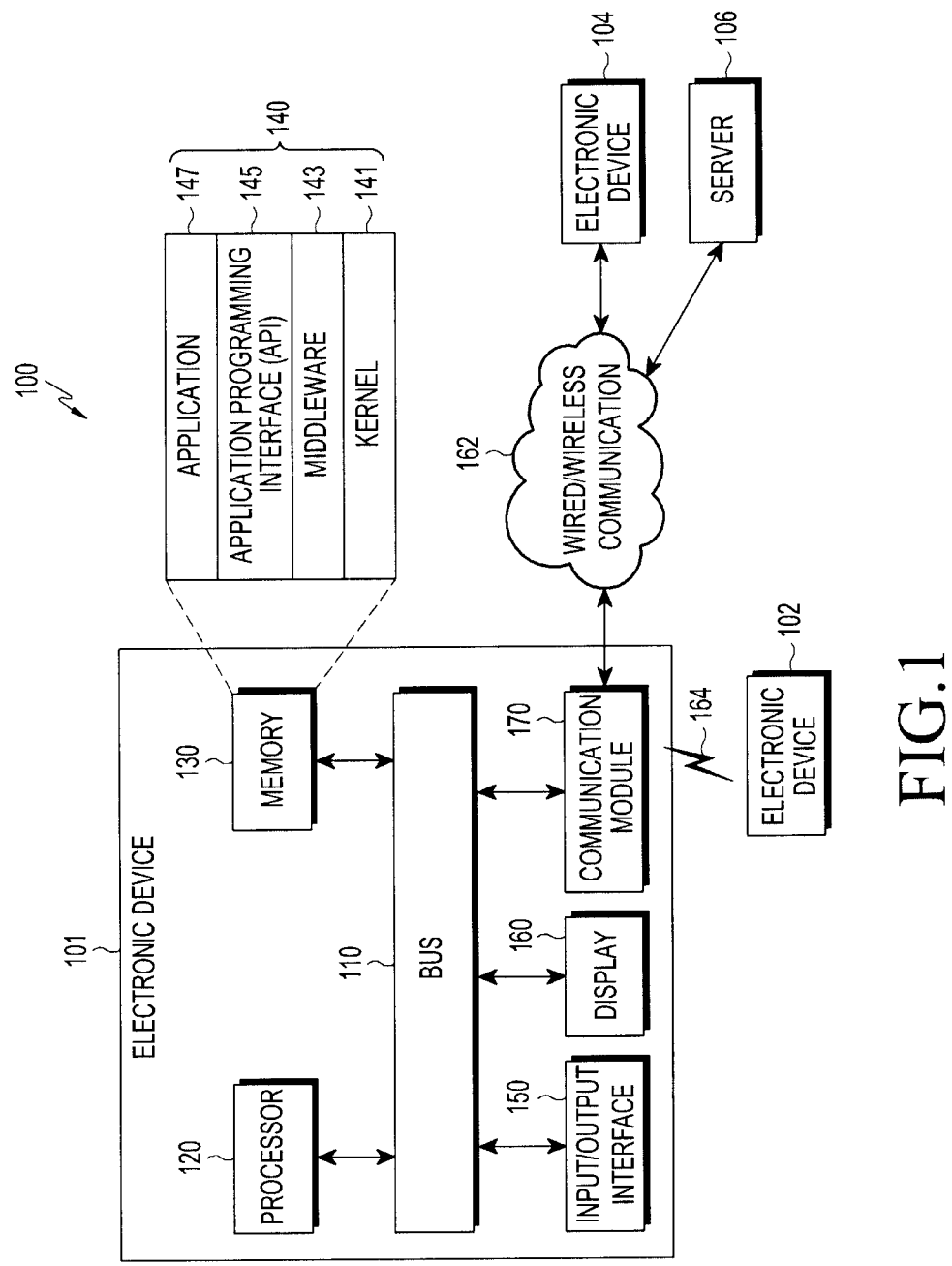
FIG. 1 is a block diagram of an example of an electronic device, according to various embodiments of the present disclosure.

Hereinafter, various embodiments of the present specification will be described with reference to the accompanying drawings. However, it should be understood that there is no intent to limit the present disclosure to the particular forms disclosed herein; rather, the present disclosure should be construed to cover various modifications, equivalents, and/or alternatives of embodiments of the present disclosure. In describing the drawings, similar reference numerals may be used to designate similar constituent elements.

As used herein, the expression "have", "may have", "include", or "may include" refers to the existence of a corresponding feature (e.g., numeral, function, operation, or constituent element such as component), and does not exclude one or more additional features.

In the present disclosure, the expression "A or B", "at least one of A or/and B", or "one or more of A or/and B" may include all possible combinations of the items listed. For example, the expression "A or B", "at least one of A and B", or "at least one of A or B" refers to all of (1) including at least one A, (2) including at least one B, or (3) including all of at least one A and at least one B.

The expression "a first", "a second", "the first", or "the second" used in various embodiments of the present disclosure may modify various components regardless of the order and/or the importance but does not limit the corresponding components. For example, a first user device and a second user device indicate different user devices although both of them are user devices. For example, a first element may be termed a second element, and similarly, a second element may be termed a first element without departing from the scope of the present disclosure.

It should be understood that when an element (e.g., first element) is referred to as being (operatively or communicatively) "connected," or "coupled," to another element (e.g., second element), it may be directly connected or coupled directly to the other element or any other element (e.g., third element) may be interposer between them. In contrast, it may be understood that when an element (e.g., first element) is referred to as being "directly connected," or "directly coupled" to another element (second element), there are no element (e.g., third element) interposed between them.

The expression "configured to" used in the present disclosure may be exchanged with, for example, "suitable for", "having the capacity to", "designed to", "adapted to", "made to", or "capable of" according to the situation. The term "configured to" may not necessarily imply "specifically designed to" in hardware. Alternatively, in some situations, the expression "device configured to" may mean that the device, together with other devices or components, "is able to". For example, the phrase "processor adapted (or configured) to perform A, B, and C" may mean a dedicated processor (e.g. embedded processor) only for performing the corresponding operations or a generic-purpose processor (e.g., central processing unit (CPU) or application processor (AP)) that can perform the corresponding operations by executing one or more software programs stored in a memory device.

The terms used herein are merely for the purpose of describing particular embodiments and are not intended to limit the scope of other embodiments. As used herein, singular forms may include plural forms as well unless the context clearly indicates otherwise. Unless defined otherwise, all terms used herein, including technical and scientific terms, have the same meaning as those commonly understood by a person skilled in the art to which the present disclosure pertains. Such terms as those defined in a generally used dictionary may be interpreted to have the meanings equal to the contextual meanings in the relevant field of art, and are not to be interpreted to have ideal or excessively formal meanings unless clearly defined in the present disclosure. In some cases, even the term defined in the present disclosure should not be interpreted to exclude embodiments of the present disclosure.

An electronic device according to various embodiments of the present disclosure may include at least one of, for example, a smart phone, a tablet Personal Computer (PC), a mobile phone, a video phone, an electronic book reader (e-book reader), a desktop PC, a laptop PC, a netbook computer, a workstation, a server, a Personal Digital Assistant (PDA), a Portable Multimedia Player (PMP), a MPEG-1 audio layer-3 (MP3) player, a mobile medical device, a camera, and a wearable device. According to various embodiments, the wearable device may include at least one of an accessory type (e.g., a watch, a ring, a bracelet, an anklet, a necklace, a glasses, a contact lens, or a Head-Mounted Device (HMD)), a fabric or clothing integrated type (e.g., an electronic clothing), a body-mounted type (e.g., a skin pad, or tattoo), and a bio-implantable type (e.g., an implantable circuit).

According to some embodiments, the electronic device may be a home appliance. The home appliance may include at least one of, for example, a television, a Digital Video Disk (DVD) player, an audio, a refrigerator, an air conditioner, a vacuum cleaner, an oven, a microwave oven, a washing machine, an air cleaner, a set-top box, a home automation control panel, a security control panel, a TV box (e.g., Samsung HomeSync™, Apple TV™, or Google TV™), a game console (e.g., Xbox™ and PlayStation™), an electronic dictionary, an electronic key, a camcorder, and an electronic photo frame.

According to another embodiment, the electronic device may include at least one of various medical devices (e.g., various portable medical measuring devices (a blood glucose monitoring device, a heart rate monitoring device, a blood pressure measuring device, a body temperature measuring device, etc.), a Magnetic Resonance Angiography (MRA), a Magnetic Resonance Imaging (MRI), a Computed Tomography (CT) machine, and an ultrasonic machine), a navigation device, a Global Positioning System (GPS) receiver, an Event Data Recorder (EDR), a Flight Data Recorder (FDR), a Vehicle Infotainment Devices, an electronic devices for a ship (e.g., a navigation device for a ship, and a gyro-compass), avionics, security devices, an automotive head unit, a robot for home or industry, an automatic teller's machine (ATM) in banks, point of sales (POS) in a shop, or internet device of things (e.g., a light bulb, various sensors, electric or gas meter, a sprinkler device, a fire alarm, a thermostat, a streetlamp, a toaster, a sporting goods, a hot water tank, a heater, a boiler, etc.).

According to some embodiments, the electronic device may include at least one of a part of furniture or a building/structure, an electronic board, an electronic signature receiving device, a projector, and various kinds of measuring instruments (e.g., a water meter, an electric meter, a gas meter, and a radio wave meter). The electronic device according to various embodiments of the present disclosure may be a combination of one or more of the aforementioned various devices. The electronic device according to some embodiments of the present disclosure may be a flexible device. Further, the electronic device according to an embodiment of the present disclosure is not limited to the aforementioned devices, and may include a new electronic device according to the development of technology.

Hereinafter, an electronic device according to various embodiments will be described with reference to the accompanying drawings. As used herein, the term "user" may indicate a person who uses an electronic device or a device (e.g., an artificial intelligence electronic device) that uses an electronic device. An electronic device 101 within a network environment 100, according to various embodiments, will be described with reference to FIG. 1. The electronic device 101 may include a bus 110, a processor 120, a memory 130, an input/output interface 150, a display 160, and a communication interface 170. In some embodiments, the electronic device 101 may omit at least one of the above elements or may further include other elements.

The bus 110 may include, for example, a circuit for connecting the elements 110 to 170 and transferring communication (e.g., control messages and/or data) between the elements.

The processor 120 may include any suitable type of processing circuitry, such as one or more general-purpose processors (e.g., ARM-based processors), a Digital Signal Processor (DSP), a Programmable Logic Device (PLD), an Application-Specific Integrated Circuit (ASIC), a Field-Programmable Gate Array (FPGA), etc. In some implementations, the processor 120 may include one or more of a Central Processing Unit (CPU), an Application Processor (AP), and a Communication Processor (CP). The processor 120, for example, may carry out operations or data processing relating to the control and/or communication of at least one other element of the electronic device 101.

The memory 130 may include any suitable type of volatile or non-volatile memory, such as Random-access Memory (RAM), Read-Only Memory (ROM), Network Accessible Storage (NAS), cloud storage, a Solid State Drive (SSD), etc. In operation, the memory 130 may include a volatile memory and/or a non-volatile memory. The memory 130 may store, for example, instructions or data relevant to at least one other element of the electronic device 101. According to an embodiment, the memory 130 may store software and/or a program 140. The program 140 may include, for example, a kernel 141, middleware 143, an Application Programming Interface (API) 145, and/or application programs (or "applications") 147. At least some of the kernel 141, the middleware 143, and the API 145 may be referred to as an Operating System (OS).

The kernel 141 may control or manage system resources (e.g., the bus 110, the processor 120, or the memory 130) used for performing an operation or a function implemented by the other programs (e.g., the middleware 143, the API 145, or the application programs 147). Furthermore, the kernel 141 may provide an interface through which the middleware 143, the API 145, or the application programs 147 may access the individual elements of the electronic device 101 to control or manage the system resources.

The middleware 143, for example, may function as an intermediary for allowing the API 145 or the application programs 147 to communicate with the kernel 141 to exchange data.

In addition, the middleware 143 may process one or more task requests received from the application programs 147 according to priorities thereof. For example, the middleware 143 may assign priorities for using the system resources (e.g., the bus 110, the processor 120, the memory 130, or the like) of the electronic device 101 to at least one of the application programs 147. For example, the middleware 143 may perform scheduling or loading balancing on the one or more task requests by processing the one or more task requests according to the priorities assigned thereto.

The API 145 is an interface through which the applications 147 control functions provided from the kernel 141 or the middleware 143, and may include, for example, at least one interface or function (e.g., instruction) for file control, window control, image processing, or text control.

The input/output interface 150, for example, may function as an interface that may transfer instructions or data input from a user or another external device to the other element(s) of the electronic device 101. Also, the input/output interface 150 may output commands or data received from other element(s) of the electronic device 101 to the user or another external device.

Examples of the display 160 may include a Liquid Crystal Display (LCD), a Light-Emitting Diode (LED) display, an Organic Light-Emitting Diode (OLED) display, a Micro-ElectroMechanical Systems (MEMS) display, and an electronic paper display. The display 160, for example, may display various types of content (e.g., text, images, videos, icons, or symbols) for the user. The display 160 may include a touch screen and receive, for example, a touch, gesture, proximity, or hovering input using an electronic pen or the user's body part.

The communication interface 170, for example, may set communication between the electronic device 101 and an external device (e.g., the first external electronic device 102, the second external electronic device 104, or a server 106). For example, the communication interface 170 may be connected to a network 162 through wireless or wired communication to communicate with the external device (e.g., the second external electronic device 104 or the server 106).

The wireless communication may use at least one of, for example, Long Term Evolution (LTE), LTE-Advance (LTE-A), Code Division Multiple Access (CDMA), Wideband CDMA (WCDMA), Universal Mobile Telecommunications System (UMTS), WiBro (Wireless Broadband), and Global System for Mobile Communications (GSM), as a cellular communication protocol. In addition, the wireless communication may include, for example, short-range communication 164. The short-range communication 164 may be performed by using at least one of, for example, Wi-Fi, Bluetooth, Near Field Communication (NFC), and Global Navigation Satellite System (GNSS). The GNSS may include at least one of, for example, a Global Positioning System (GPS), a Global Navigation Satellite System (Glonass), a Beidou Navigation Satellite System (hereinafter referred to as "Beidou"), and a European Global Satellite-based Navigation System (Galileo), according to a use area, a bandwidth, or the like. Hereinafter, "GPS" may be interchangeably used with "GNSS". The wired communication may include at least one of, for example, a Universal Serial Bus (USB), a High Definition Multimedia Interface (HDMI), Recommended Standard 232 (RS-232), and a Plain Old Telephone Service (POTS). The network 162 may include at least one of a communication network such as a computer network (e.g., a LAN or a WAN), the Internet, and a telephone network.

Each of the first and second external electronic devices 102 and 104 may be of a type that is identical to or different from that of the electronic device 101. According to an embodiment, the server 106 may include a group of one or more servers. According to various embodiments, all or some of the operations performed in the electronic device 101 may be performed in another electronic device or a plurality of electronic devices (e.g., the electronic devices 102 and 104 or the server 106). According to an embodiment, when the electronic device 101 has to perform some functions or services automatically or in response to a request, the electronic device 101 may make a request for performing at least some functions relating thereto to another device (e.g., the electronic device 102 or 104 or the server 106) instead of performing the functions or services by itself or in addition. Another electronic device (for example, the electronic devices 102 and 104, or the server 106) may execute the requested functions or the additional functions, and may deliver a result of the execution to the electronic device 101. The electronic device 101 may process the received result as it is or additionally to provide the requested functions or services. To achieve this, for example, cloud computing, distributed computing, or client-server computing technology may be used.

In various embodiments of the present disclosure, the display 160 may display a sleep information input screen determined according to a sleep pattern. The input/output interface 150 may obtain sleep information corresponding to the sleep information input screen. The processor 120 may control the obtained sleep information to be stored in the memory 130.

In various embodiments of the present disclosure, the sleep pattern includes a bedtime for reference and a wake-up time for reference, and the processor 120 may control the sleep information input screen including the bedtime for reference and the wake-up time for reference to be displayed on a screen.

In various embodiments of the present disclosure, the processor 120 may control a bedtime input window and a wake-up time input window to be displayed, the bedtime for reference to be set and displayed as an initial value of the bedtime input window and display the bedtime input window, and the wake-up time for reference to be set and displayed as an initial value of the wake-up time input window.

In various embodiments of the present disclosure, the processor 120 may obtain the time set in each of the bedtime input window and the wake-up time input window as the sleep information.

In various embodiments of the present disclosure, the processor 120 may obtain data sensed by a sensor, and determine the sleep pattern based on the sensed data. The sensed data may contain at least one of a step count, movement information of the electronic device, skin hydration information, Blood pressure information, Heart Rate (HR) information, Electroencephalogram (EEG) information, Electrocardiogram (ECG) information, Electromyograph (EMG) information, Electrooculogram (EOG) information, body temperature information, and noise information.

In various embodiments of the present disclosure, the processor 120 may determine the sleep pattern based on pre-stored sleep information.

In various embodiments of the present disclosure, the processor 120 may determine the sleep pattern based on finally stored sleep information.

In various embodiments of the present disclosure, the processor 120 may determine the sleep pattern based on designated sleep information.

In various embodiments of the present disclosure, the processor 120 may determine the sleep pattern based on a weighted average for sleep information during a predetermined period.

In various embodiments of the present disclosure, the processor 120 may determine an execution time of a sleep information management application and determine the sleep pattern based on the sleep pattern and the execution time.

In various embodiments of the present disclosure, the processor 120 may set a section according to the sleep pattern, determine a first section, to which the execution time belongs, and control the sleep information input screen to be displayed based on the first section and the sleep pattern.

In various embodiments of the present disclosure, the processor 120 may determine an input target date of the sleep information according to the execution time.

In various embodiments of the present disclosure, the processor 120 may determine the sleep pattern based on at least one of an obtainment time of an execution command for an application, a release time of an alarm application, information input into a schedule management application, a turn-on time of the display 160 included in the electronic device, a turn-off time of the display 160, and an unlock time of the electronic device 101.

In various embodiments of the present disclosure, the communication interface 170 may receive data from other electronic devices 102 and 104. The processor 120 may determine the sleep pattern based on data received from other electronic devices.

In various embodiments of the present disclosure, the processor 120 may obtain location information of the electronic device and determine the sleep pattern based on the location information.

In various embodiments of the present disclosure, the processor 120 may confirm a user of the electronic device 101 and determine the sleep pattern in response to the confirmed user.

Figure 2:
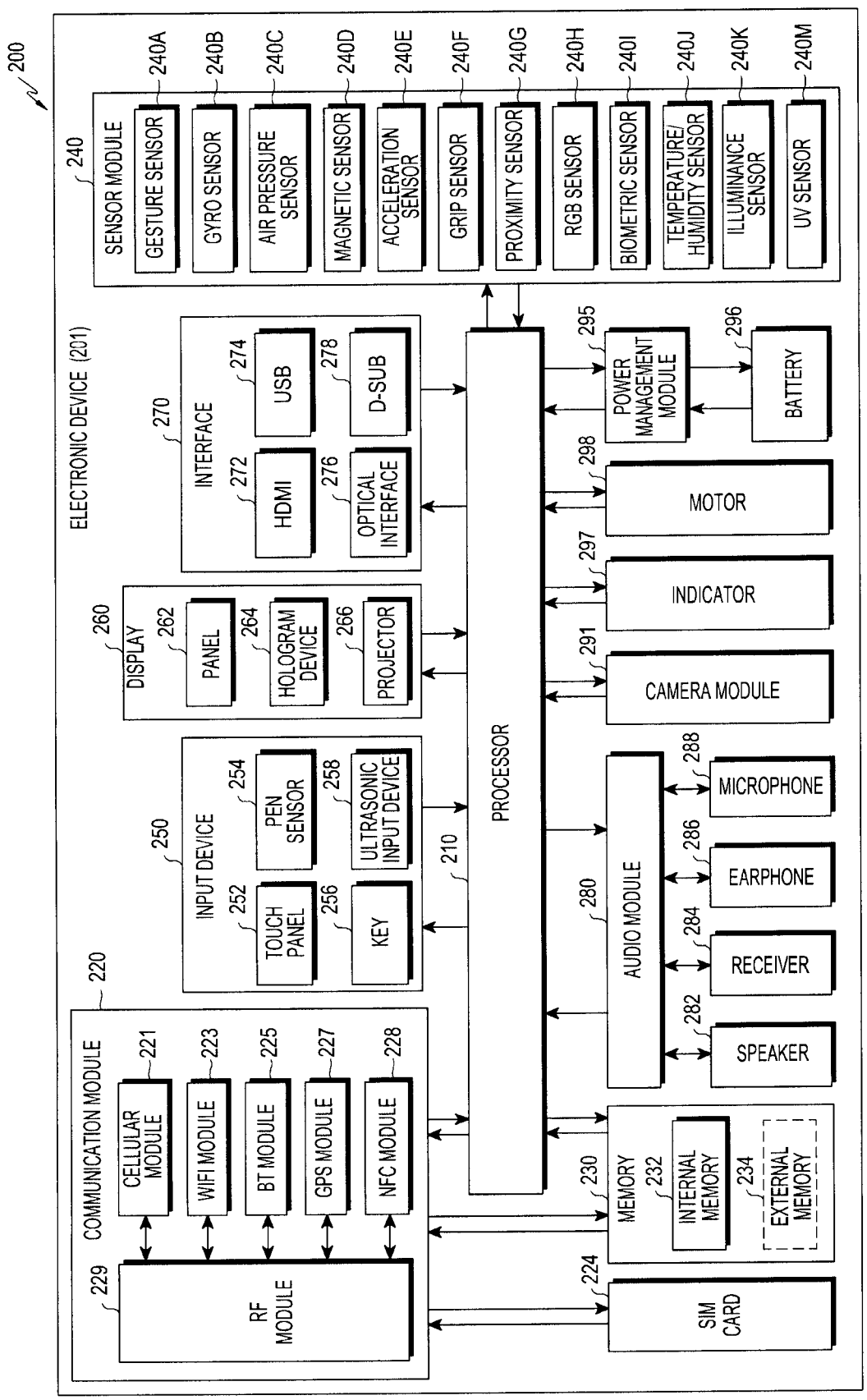
FIG. 2 is a block diagram of an example of an electronic device according to various embodiments.

FIG. 2 is a block diagram of an electronic device 201 according to various embodiments. For example, the electronic device 201 may include the whole or part of the electronic device 101 illustrated in FIG. 1. The electronic device 201 may include at least one Application Processor (AP) 210, a communication module 220, a Subscriber Identification Module (SIM) card 224, a memory 230, a sensor module 240, an input device 250, a display 260, an interface 270, an audio module 280, a camera module 291, a power management module 295, a battery 296, an indicator 297, and a motor 298.

The processor 210 may control a plurality of hardware or software components connected to the processor 210 by driving an operating system or an application program and perform the processing of various pieces of data and calculations. The processor 210 may be implemented by, for example, a System on Chip (SoC). According to an embodiment, the processor 210 may further include a Graphic Processing Unit (GPU) and/or an image signal processor. The processor 210 may include at least some (e.g., a cellular module 221) of the elements illustrated in FIG. 2. The processor 210 may load, into a volatile memory, instructions or data received from at least one (e.g., a non-volatile memory) of the other elements and may process the loaded instructions or data, and may store various data in a non-volatile memory.

The communication module 220 may have a configuration equal or similar to that of the communication interface 170 of FIG. 1. The communication module 220 may include, for example, the cellular module 221, a Wi-Fi module 223, a Bluetooth (BT) module 225, a GNSS module 227 (e.g., a GPS module, a Glonass module, a Beidou module, or a Galileo module), an NFC module 228, and a Radio Frequency (RF) module 229.

The cellular module 221 may provide a voice call, image call, a text message service, or an Internet service through, for example, a communication network. According to an embodiment, the cellular module 221 may distinguish between and authenticate electronic devices 201 within a communication network using a subscriber identification module (for example, the SIM card 224). According to an embodiment of the present disclosure, the cellular module 221 may perform at least some of the functions that the processor 210 may provide. According to an embodiment, the cellular module 221 may include a Communication Processor (CP).

Each of the Wi-Fi module 223, the BT module 225, the GNSS module 227, and the NFC module 228 may include, for example, a processor for processing data transmitted and received through the relevant module. According to a specific embodiment, at least some (two or more) of the cellular module 221, the WiFi module 223, the Bluetooth module 225, the GPS module 227, and the NFC module 228 may be included in one Integrated Chip (IC) or IC package.

The RF module 229 may transmit/receive, for example, a communication signal (for example, an RF signal). The RF module 229 may include, for example, a transceiver, a Power Amp Module (PAM), a frequency filter, a Low Noise Amplifier (LNA), or an antenna. According to another embodiment, at least one of the cellular module 221, the WiFi module 223, the BT module 225, the GPS module 227, and the NFC module 228 may transmit/receive an RF signal through a separate RF module.

The subscriber identification module 224 may include, for example, a card including a subscriber identity module and/or an embedded SIM, and may contain unique identification information (e.g., an Integrated Circuit Card Identifier (ICCID)) or subscriber information (e.g., an International Mobile Subscriber Identity (IMSI)).

The memory 230 (for example, the memory 130) may include, for example, an internal memory 232 or an external memory 234. The embedded memory 232 may include at least one of a volatile memory (for example, a Dynamic Random Access Memory (DRAM), a Static RAM (SRAM), a Synchronous Dynamic RAM (SDRAM), and the like) and a non-volatile memory (for example, a One Time Programmable Read Only Memory (OTPROM), a Programmable ROM (PROM), an Erasable and Programmable ROM (EPROM), an Electrically Erasable and Programmable ROM (EEPROM), a mask ROM, a flash ROM, a flash memory (for example, a NAND flash memory or a NOR flash memory), a hard disc drive, a Solid State Drive (SSD), and the like).

An external memory 234 may further include a flash drive, for example, a Compact Flash (CF), a Secure Digital (SD), a Micro Secure Digital (Micro-SD), a Mini Secure Digital (Mini-SD), an eXtreme Digital (xD), a memory stick, or the like. The external memory 234 may be functionally and/or physically connected to the electronic device 201 through various interfaces.

The sensor module 240 may measure a physical quantity or detect an operation state of the electronic device 201, and may convert the measured or detected information into an electrical signal. The sensor module 240 may include, for example, at least one of a gesture sensor 240A, a gyro sensor 240B, an atmospheric pressure sensor 240C, a magnetic sensor 240D, an acceleration sensor 240E, a grip sensor 240F, a proximity sensor 240G, a color sensor 240H (for example, a red, green, blue (RGB) sensor), a biometric sensor 240I, a temperature/humidity sensor 240J, a light sensor 240K, and a ultraviolet (UV) sensor 240M. Additionally or alternatively, the sensor module 240 may include, for example, an E-nose sensor, an electromyography (EMG) sensor, an electroencephalogram (EEG) sensor, an electrocardiogram (ECG) sensor, an Infrared (IR) sensor, an iris sensor, and/or a fingerprint sensor. The sensor module 240 may further include a control circuit for controlling one or more sensors included therein. In some embodiments of the present disclosure, an electronic device 201 may further include a processor configured to control the sensor module 240 as a part of or separately from the processor 210, and may control the sensor module 240 while the processor 210 is in a sleep state.

The input device 250 may include, for example, a touch panel 252, a (digital) pen sensor 254, a key 256, or an ultrasonic input device 258. The touch panel 252 may use at least one of, for example, a capacitive type, a resistive type, an infrared type, and an ultrasonic type. Also, the touch panel 252 may further include a control circuit. The touch panel 252 may further include a tactile layer and provide a tactile reaction to the user.

The (digital) pen sensor 254 may include, for example, a recognition sheet which is a part of the touch panel or is separated from the touch panel. The key 256 may include, for example, a physical button, an optical key or a keypad. The ultrasonic input device 258 may detect ultrasonic waves generated by an input tool through a microphone (for example, a microphone 288) and identify data corresponding to the detected ultrasonic waves.

The display 260 (for example, the display 160) may include a panel 262, a hologram device 264 or a projector 266. The panel 262 may include a configuration identical or similar to that of the display 160 illustrated in FIG. 1. The panel 262 may be implemented to be, for example, flexible, transparent, or wearable. The panel 262 and the touch panel 252 may be implemented as one module. The hologram 264 may show a three-dimensional image in the air by using an interference of light. The projector 266 may display an image by projecting light onto a screen. The screen may be located, for example, inside or outside the electronic device 201. According to an embodiment, the display 260 may further include a control circuit for controlling the panel 262, the hologram device 264, or the projector 266.

The interface 270 may include, for example, a High-Definition Multimedia Interface (HDMI) 272, a Universal Serial Bus (USB) 274, an optical interface 276, or a D-sub-miniature (D-sub) 278. The interface 270 may be included in, for example, the communication interface 170 illustrated in FIG. 1. Additionally or alternatively, the interface 270 may include, for example, a Mobile High-definition Link (MHL) interface, a Secure Digital (SD) card/Multi-Media Card (MMC) interface, or an Infrared Data Association (IrDA) standard interface.

The audio module 280 may bilaterally convert, for example, a sound and an electrical signal. At least some elements of the audio module 280 may be included in, for example, the input/output interface 150 illustrated in FIG. 1. The audio module 280 may process sound information that is input or output through, for example, a speaker 282, a receiver 284, earphones 286, the microphone 288 or the like.

The camera module 291 is a device that may photograph a still image and a dynamic image. According to an embodiment, the camera module 291 may include one or more image sensors (for example, a front sensor or a back sensor), a lens, an Image Signal Processor (ISP) or a flash (for example, LED or xenon lamp).

The power management module 295 may manage, for example, power of the electronic device 201. According to an embodiment, the power management module 295 may include a Power Management Integrated Circuit (PMIC), a charger Integrated Circuit (IC), or a battery or fuel gauge. The PMIC may use a wired and/or wireless charging method. Examples of the wireless charging method may include, for example, a magnetic resonance method, a magnetic induction method, an electromagnetic wave method, and the like. Additional circuits (e.g., a coil loop, a resonance circuit, a rectifier, etc.) for wireless charging may be further included. The battery gauge may measure, for example, a residual quantity of the battery 296, and a voltage, a current, or a temperature during the charging. The battery 296 may include, for example, a rechargeable battery or a solar battery.

The indicator 297 may display a particular state (e.g., a booting state, a message state, a charging state, or the like) of the electronic device 201 or a part (e.g., the processor 210) of the electronic device 201. The motor 298 may convert an electrical signal into mechanical vibration, and may generate a vibration, a haptic effect, or the like. Although not illustrated, the electronic device 201 may include a processing unit (e.g., a GPU) for supporting mobile television (TV). The processing unit for supporting mobile TV may, for example, process media data according to a certain standard such as Digital Multimedia Broadcasting (DMB), Digital Video Broadcasting (DVB), or media-FLO™.

Each of the above-described component elements of hardware according to the present disclosure may be configured with one or more components, and the names of the corresponding component elements may vary based on the type of electronic device. The electronic device according to various embodiments of the present disclosure may include at least one of the aforementioned elements. Some elements may be omitted or other additional elements may be further included in the electronic device. Also, some of the hardware components according to various embodiments may be combined into one entity, which may perform functions identical to those of the relevant components before the combination.

Figure 3:
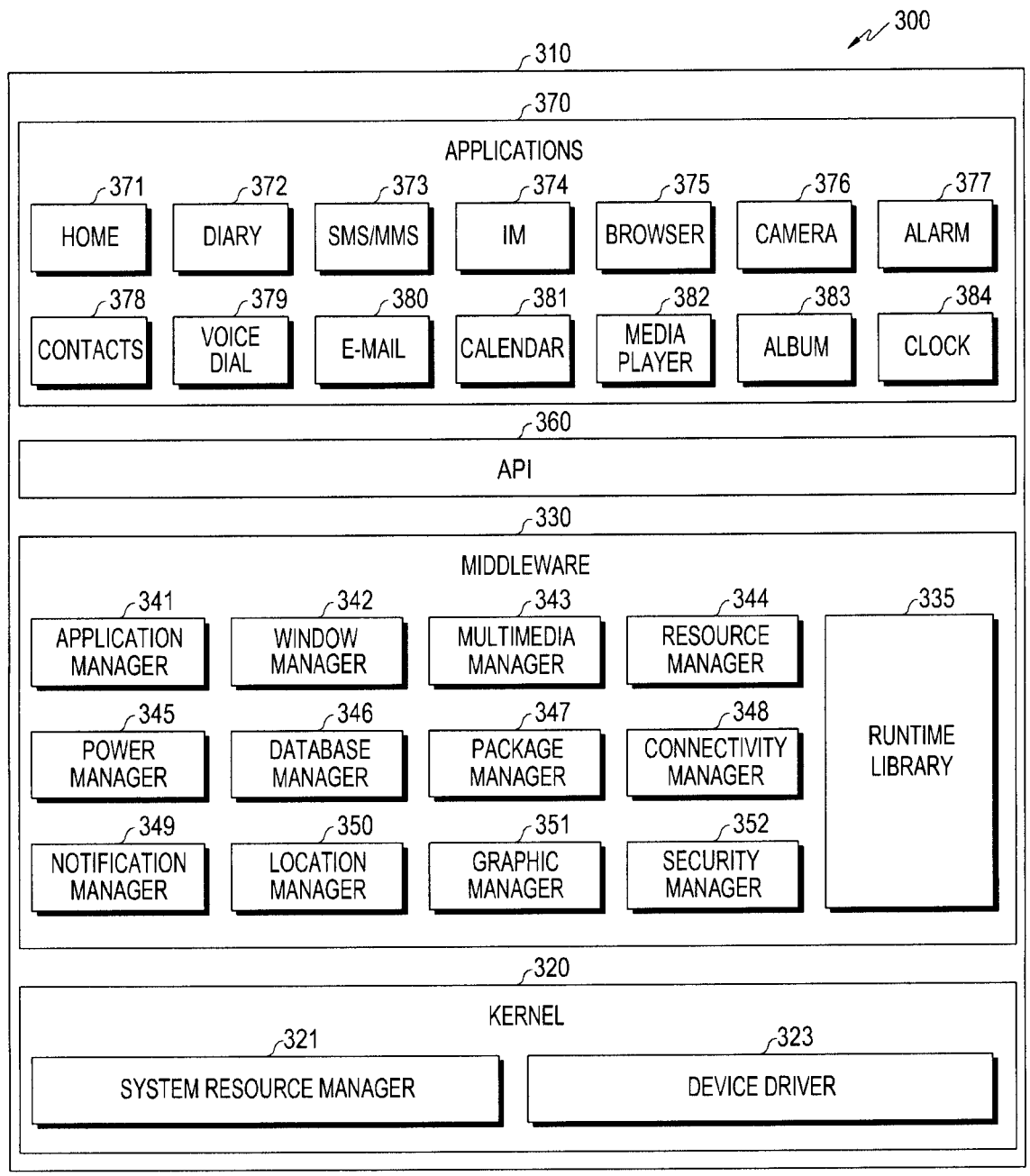
FIG. 3 is a block diagram of an example of a program module, according to various embodiments.

FIG. 3 is a block diagram of a program module according to various embodiments. According to an embodiment, the program module 310 (for example, the program 140) may include an Operating System (OS) for controlling resources related to the electronic device (for example, the electronic device 101) and/or various applications (for example, the application programs 147) executed in the operating system. The operating system may be, for example, Android, iOS, Windows, Symbian, Tizen, Bada, or the like.

The program module 310 may include a kernel 320, middleware 330, an Application Programming Interface (API) 360, and/or an application 370. At least some of the program module 310 may be preloaded on the electronic device, or may be downloaded from an external electronic device (e.g., the electronic device 102 or 104, or the server 106).

The kernel 320 (for example, the kernel 141) may include, for example, a system resource manager 321 and/or a device driver 323. The system resource manager 321 may perform the control, allocation, retrieval, or the like of system resources. According to an embodiment of the present disclosure, the system resource manager 321 may include a process manager, a memory manager, a file system manager, or the like. The device driver 323 may include, for example, a display driver, a camera driver, a Bluetooth driver, a shared memory driver, a USB driver, a keypad driver, a Wi-Fi driver, an audio driver, or an Inter-Process Communication (IPC) driver.

The middleware 330 may provide a function required by the applications 370 in common or may provide various functions to the applications 370 through the API 360 so that the applications 370 can efficiently use limited system resources within the electronic device. According to an embodiment, the middleware 330 (for example, the middleware 143) may include, for example, at least one of a runtime library 335, an application manager 341, a window manager 342, a multimedia manager 343, a resource manager 344, a power manager 345, a database manager 346, a package manager 347, a connectivity manager 348, a notification manager 349, a location manager 350, a graphic manager 351, and a security manager 352.

The runtime library 335 may include a library module which a compiler uses in order to add a new function through a programming language while the applications 370 are being executed. The runtime library 335 may perform input/output management, memory management, the functionality for an arithmetic function, or the like.

The application manager 341 may manage, for example, the life cycle of at least one of the applications 370. The window manager 342 may manage Graphical User Interface (GUI) resources used for the screen. The multimedia manager 343 may determine a format required to reproduce various media files, and may encode or decode a media file by using a coder/decoder (codec) appropriate for the corresponding format. The resource manager 344 may manage resources, such as a source code, a memory, a storage space, and the like of at least one of the applications 370.

The power manager 345 may operate together with a Basic Input/Output System (BIOS) to manage a battery or power, and may provide power information required for the operation of the electronic device. The database manager 346 may generate, search for, and/or change a database to be used by at least one of the applications 370. The package manager 347 may manage the installation or update of an application distributed in the form of a package file.

The connectivity manager 348 may manage a wireless connection such as, for example, Wi-Fi or Bluetooth. The notification manager 349 may display or notify of an event, such as an arrival message, an appointment, a proximity notification, and the like, in such a manner so as not to disturb the user. The location manager 350 may manage location information of the electronic device. The graphic manager 351 may manage a graphic effect, which is to be provided to the user, or a user interface related to the graphic effect. The security manager 352 may provide various security functions required for system security, user authentication, and the like. According to an embodiment of the present disclosure, when the electronic device (for example, the electronic device 101) has a telephone call function, the middleware 330 may further include a telephony manager for managing a voice call function or a video call function of the electronic device.

The middleware 330 may include a middleware module that forms a combination of various functions of the above-described elements. The middleware 330 may provide a module specialized for each type of OS in order to provide a differentiated function. Also, the middleware 330 may dynamically delete some of the existing elements, or may add new elements.

The API 360 (for example, the API 145) is, for example, a set of API programming functions, and may be provided with a different configuration according to an OS. For example, in the case of Android or iOS, one API set may be provided for each platform. In the case of Tizen, two or more API sets may be provided for each platform.

The applications 370 (for example, the application program 147) may include, for example, one or more applications which can provide functions such as home 371, dial 372, SMS/MMS 373, Instant Message (IM) 374, browser 375, camera 376, alarm 377, contacts 378, voice dialer 379, email 380, calendar 381, media player 382, album 383, clock 384, health care (for example, measure exercise quantity or blood sugar), or environment information (for example, atmospheric pressure, humidity, or temperature information).

According to an embodiment of the present disclosure, the applications 370 may include an application (hereinafter, referred to as an "information exchange application" for the convenience of description) supporting information exchange between the electronic device (e.g., the electronic device 101) and an external electronic device (e.g., the electronic device 102 or 104). The information exchange application may include, for example, a notification relay application for transferring specific information to an external electronic device or a device management application for managing an external electronic device.

For example, the notification relay application may include a function of transferring, to the external electronic device (for example, the electronic device 102 or 104), notification information generated from other applications of the electronic device 101 (for example, an SMS/MMS application, an e-mail application, a health management application, or an environmental information application). Further, the notification relay application may receive notification information from, for example, an external electronic device and provide the received notification information to a user.

The device management application may manage (for example, install, delete, or update), for example, a function for at least a part of the external electronic device (for example, the electronic device 102 or 104) communicating with the electronic device (for example, turning on/off the external electronic device itself (or some elements thereof) or adjusting brightness (or resolution) of a display), applications executed in the external electronic device, or services provided from the external electronic device (for example, a telephone call service or a message service).

According to an embodiment, the applications 370 may include applications (for example, a health care application of a mobile medical appliance or the like) designated according to attributes of the external electronic device 102 or 104. According to an embodiment of the present disclosure, the application 370 may include an application received from the external electronic device (e.g., the server 106, or the electronic device 102 or 104). According to an embodiment of the present disclosure, the application 370 may include a preloaded application or a third party application which can be downloaded from the server. Names of the elements of the program module 310, according to the above-described embodiments of the present disclosure, may change depending on the type of OS.

According to various embodiments of the present disclosure, at least some of the program module 310 may be implemented in software, firmware, hardware, or a combination of two or more thereof. At least some of the program module 310 may be implemented (e.g., executed) by, for example, the processor (e.g., the processor 210). At least some of the program module 310 may include, for example, a module, a program, a routine, a set of instructions, and/or a process for performing one or more functions.

The term "module" as used herein may, for example, mean a unit including one of hardware, software, and firmware or a combination of two or more of them. The "module" may be interchangeably used with, for example, the term "unit", "logic", "logical block", "component", or "circuit". The "module" may be a minimum unit of an integrated component element or a part thereof. The "module" may be a minimum unit for performing one or more functions or a part thereof. The "module" may be mechanically or electronically implemented. For example, the "module" according to the present disclosure may include at least one of an Application-Specific Integrated Circuit (ASIC) chip, a Field-Programmable Gate Arrays (FPGA), and a programmable-logic device for performing operations which have been known or are to be developed hereinafter.

According to various embodiments, at least some of the devices (for example, modules or functions thereof) or the method (for example, operations) according to the present disclosure may be implemented by a command stored in a computer-readable storage medium in a programming module form. The instruction, when executed by a processor (e.g., the processor 120), may cause the one or more processors to execute the function corresponding to the instruction. The computer-readable storage medium may be, for example, the memory 130.

The computer readable recoding medium may include a hard disk, a floppy disk, magnetic media (e.g., a magnetic tape), optical media (e.g., a Compact Disc Read Only Memory (CD-ROM) and a Digital Versatile Disc (DVD)), magneto-optical media (e.g., a floptical disk), a hardware device (e.g., a Read Only Memory (ROM), a Random Access Memory (RAM), a flash memory), and the like. In addition, the program instructions may include high-class language codes, which can be executed in a computer by using an interpreter, as well as machine codes made by a compiler. The aforementioned hardware device may be configured to operate as one or more software modules in order to perform the operation of the present disclosure, and vice versa.

The programming module according to the present disclosure may include one or more of the aforementioned components or may further include other additional components, or some of the aforementioned components may be omitted. Operations executed by a module, a programming module, or other component elements according to various embodiments of the present disclosure may be executed sequentially, in parallel, repeatedly, or in a heuristic manner. Further, some operations may be executed according to another order or may be omitted, or other operations may be added. Various embodiments disclosed herein are provided merely to easily describe technical details of the present disclosure and to help the understanding of the present disclosure and are not intended to limit the scope of the present disclosure. Accordingly, the scope of the present disclosure should be construed as including all modifications or various other embodiments based on the technical idea of the present disclosure.

Figure 4:
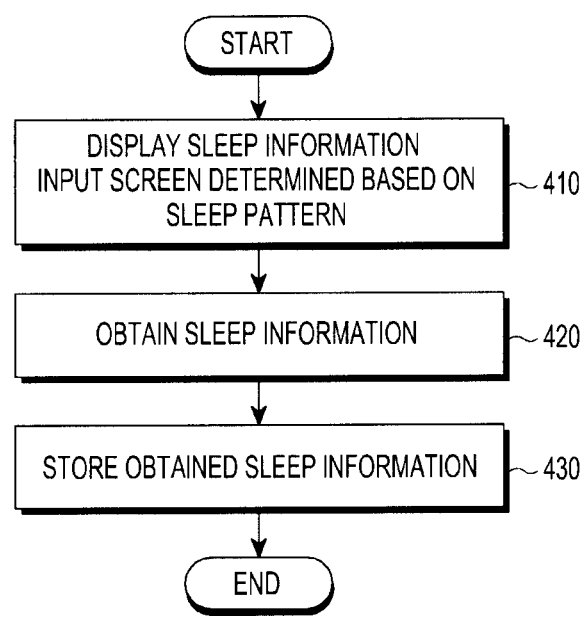
FIG. 4 is a flowchart of an example of a process, according to various embodiments of the present disclosure.

FIG. 4 is a flowchart of an example of a process, according to various embodiments of the present disclosure.

In operation 410, the electronic device 101 may display a sleep information input screen determined based on a sleep pattern. Here, the sleep pattern may include a bedtime, a wake-up time, a sleeping time, and sleep efficiency of a user of the electronic device 101. For example, the sleep pattern may be represented in Table 1 below.

TABLE 1

| User | Bedtime | Wake-up time | Sleeping time | Sleeping efficiency |
|---|---|---|---|---|
| First user | 12:40 AM | 7:20 AM | 6 h 40 min | 85% |
| Second user | 12:10 AM | 6:30 AM | 6 h 20 min | 75% |

As illustrated, the electronic device 101 may store in Table 1 an indication that a first user sleeps for 6 hours and 40 minutes from 12:40 AM to 7:20 AM with a sleep efficiency of 85%. Further, the electronic device 101 may store in Table 1 an indication that the second user sleeps for 6 hours and 20 minutes from 12:10 AM to 6:30 AM with sleep efficiency of 75%. In some implementations, the sleep efficiency may be the proportion of deep sleep time out of the total time a user has spent sleeping. In various embodiments of the present disclosure, the electronic device 101 may measure the sleep efficiency based on various sensed data, such as movement information and a bio-signal.

The electronic device 101 may determine a sleep pattern by using pre-stored sleep information. The electronic device 101 may determine a sleep pattern by using sensed data from various included sensors. The electronic device 101 may determine a sleep pattern by using location information of the electronic device 101. The electronic device 101 may determine a sleep pattern by using an execution time of the sleep information management application. The electronic device 101 may determine a sleep pattern by using information received from another electronic device. The information may be obtained via a wired or wireless connection between the electronic device 101 and the other electronic device. The electronic device 101 may determine a sleep pattern by using use information of the electronic device 101. The electronic device 101 may determine a sleep pattern by using user schedule information. Otherwise, the electronic device 101 may also determine a sleep pattern by using a combination of the aforementioned various information.

The electronic device 101 may display a sleep information input screen determined based on the sleep pattern. In various embodiments of the present disclosure, the electronic device 101 may insert a bedtime and a wake-up time of the sleep pattern into the sleep information input screen and display the bedtime and the wake-up time of the sleep pattern. According to aspects of the disclosure, the bedtime and the wake-up time of the sleep pattern may be referred to as "sleep information" For example, the electronic device 101 may display sleep information for reference which the user may refer to input the sleep information. The sleep information for reference may include, for example, a wake-up time for reference and a bedtime for reference. That is, in one embodiment, the electronic device 101 may display the sleep information input screen including a wake-up time for reference and a bedtime for reference.

The sleep information input screen may include one or more objects as a graphic user interface. The electronic device 101 may include the sleep information management application, and the sleep information input screen may be an execution screen of the sleep information management application. When each of one or more objects of the sleep information input screen is designated, the electronic device 101 may serve a function corresponding to each object. In one embodiment, the sleep information input screen may include a bedtime input object and a wake-up time input object, and the sleep information for reference may be an initial value of the sleep information input screen.

The bedtime input object and the wake-up time input object may be implemented by a bedtime input window and a wake-up time input window.

In operation 420, the electronic device 101 may obtain sleep information. In one embodiment, the sleep information input screen may further include an adjustment object capable of adjusting a bedtime and a wake-up time. The adjustment object may include a button, and/or any other suitable type of input component. Accordingly, when the adjustment object is activated (e.g., pressed), the electronic device 101 may receive an input of the sleep information containing at least one of the wake-up time and the bedtime. In this case, the user adjusts the sleep information from the sleep information for reference that is the initial value, thereby more easily inputting the sleep information. In another embodiment, when the sleep information for reference is accurate, the user may input a command for saving the sleep information, and the electronic device 101 may store the sleep information for reference as sleep information that is associated with a corresponding date.

In operation 430, the electronic device 101 may store the obtained sleep information. As described above, the electronic device 101 may obtain the sleep information for reference or the sleep information adjusted from the sleep information for reference, and store the obtained sleep information. The electronic device 101 may establish a date-based sleep information database. The electronic device 101 may analyze the sleep information that is stored in the database. Otherwise, the electronic device 101 may also update the sleep pattern by using the established database. In this case, when the electronic device 101 re-executes the operation 410, the electronic device 101 may also display the sleep information input screen determined based on the updated sleep pattern.

FIGS. 5A to 5H are diagrams of different examples of user interfaces, according to various embodiments of the present disclosure.

Figure 5A:
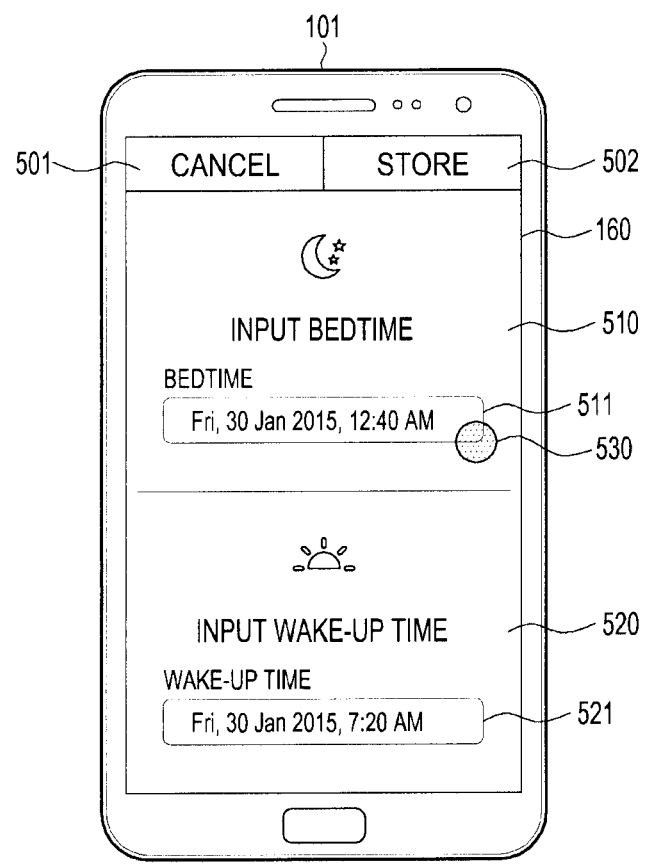
FIG. 5A is a diagram of an example of a user interface, according to various embodiments of the present disclosure.

Referring to FIG. 5A, the electronic device 101 may display the sleep information input screen on a display 500. In the embodiments of FIGS. 5A to 5D, the electronic device 101 is illustrated as a mobile electronic device, such as a smartphone, but is simply for illustrative purposes, and as described above, the electronic device 101 may be implemented by a wearable device and the like, and the kind of thereof is not limited.

In various embodiments of the present disclosure, the sleep information input screen may include a bedtime input screen 510 and a wake-up input screen 520. A bedtime interface component 511 may be included in the bedtime input screen 510, and a wake-up time interface component 521 may be included in the wake-up time input screen 520. As described above, the electronic device 101 may store a sleep pattern. The electronic device 101 may determine the sleep pattern based on various data, such as sensed data and pre-stored sleep information as described above. In the embodiment of FIG. 5A, the electronic device 101 may store the sleep pattern including a bedtime of 12:40 AM and a wake-up time of 7:20 AM. Accordingly, the electronic device 101 may display the bedtime interface component 511 and the wake-up time 521 interface component by using the sleep pattern. The sleep information input screen may include a cancel object 501 and a storage object 502. When the cancel object 501 is designated, the electronic device 101 may cancel corresponding input information and display a sleep information confirming screen. The sleep information confirming screen will be described in more detail below. Additionally or alternatively, the electronic device 101 may also display an input target date when displaying the sleep information for reference 511 and 521. In the embodiment of FIG. 5A, the electronic device 101 may determine the input target date as Friday, Jan. 30, 2015, and further display the determined input target date. A configuration of determining the input target date by the electronic device 101 will be described in more detail below.

In the embodiment of FIG. 5A, a user may confirm the sleep information for interface components 511 and 521 and input sleep information corresponding to the sleep information for interface components 511 and 521. For example, when the sleep information that is entered in the interface components 511 and 521 corresponds to a value desired to be actually input, the user may activate (e.g., press) the storage object 502. The electronic device 101 may store sleep information displayed when the storage object 502 is activated. In some implementations, the electronic device 101 may store the sleep information entered in the interface components 511 and 521 as sleep information corresponding to a particular target date, for example, Friday, Jan. 30, 2015. In some implementations, the user may determine that the sleep information that is entered in the input components 511 and 521 does not correspond to the value desired to be actually input, and input an adjustment command 530. As illustrated, the input adjustment command may be input by performing a touch on one of the interface components 511 and 521

Figure 5B:
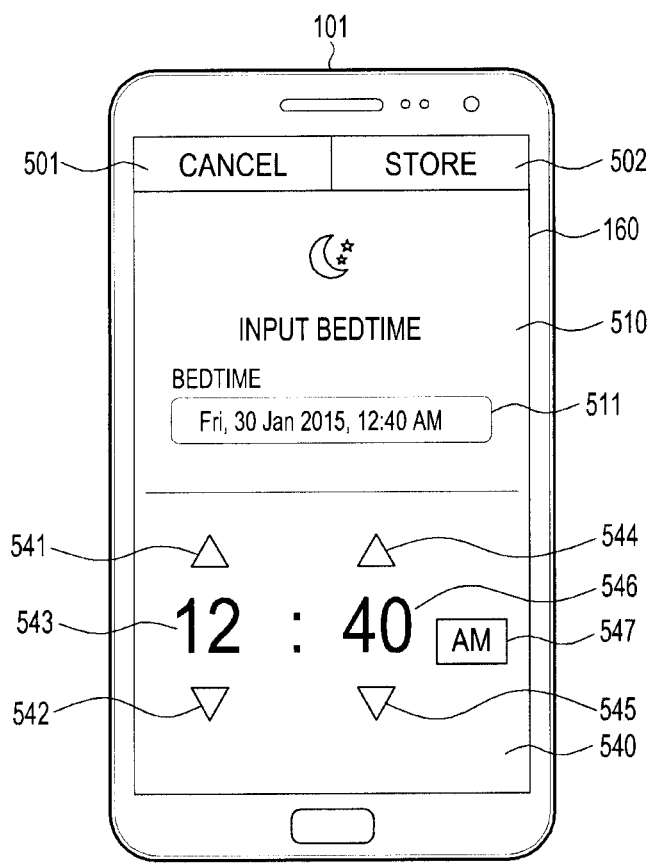
FIG. 5B is a diagram of an example of a user interface, according to various embodiments of the present disclosure.

When the adjustment command 530 is input, the electronic device 101 may display the sleep information input screen adjustable the sleep information as illustrated in FIG. 5B.

The sleep information input screen according to various embodiments of the present disclosure may include a sleep information adjustment window 540. Hour-unit adjustment objects 541, 542, and 543, minute-unit adjustment object 544, 545, and 546, and a am/pm switch object 547 may be included in the sleep information adjustment window 540. When the hour-unit adjustment object 541 is activated (e.g., touched), the electronic device 101 may increase the number indicated by the hour-unit adjustment object 543, and when the hour-unit adjustment object 542 is activated, the electronic device 101 may decrease the number indicated by the hour-unit adjustment object 543. When the minute-unit adjustment object 544 is activated, the electronic device 101 may increase the number indicated by the minute-unit adjustment object 546, and when the minute-unit adjustment object 545 is activated, the electronic device 101 may decrease the number indicated by the minute-unit adjustment object 546. When the am/pm switch object 547 is activated, the electronic device 101 may change the period of the day that is indicated by the am/pm switch object 547. The user may input the sleep information by manipulating the hour-unit adjustment objects 541, 542, and 543, the minute-unit adjustment object 544, 545, and 546, and the am/pm switch object 547.

Figure 5C:
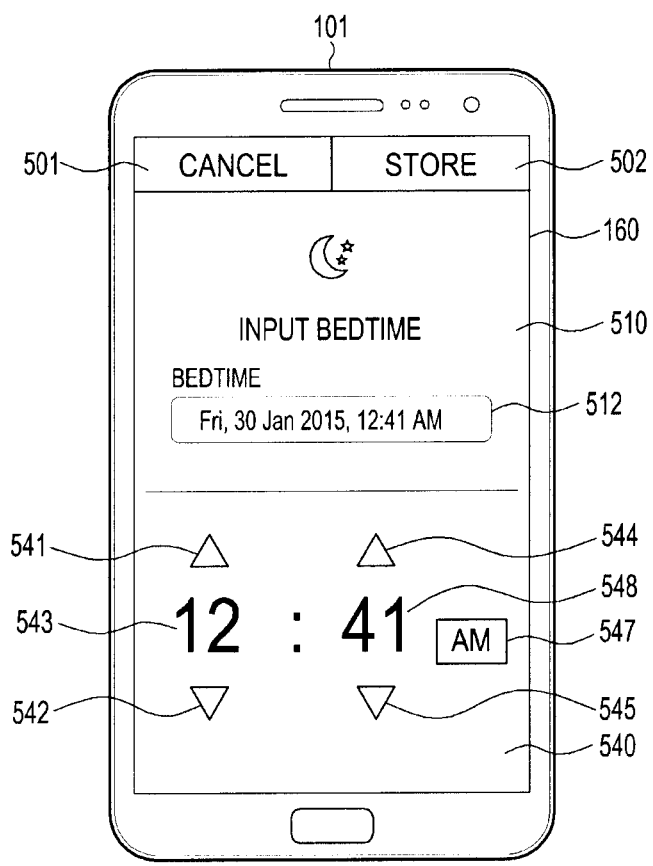
FIG. 5C is a diagram of an example of a user interface, according to various embodiments of the present disclosure.
Figure 5D:
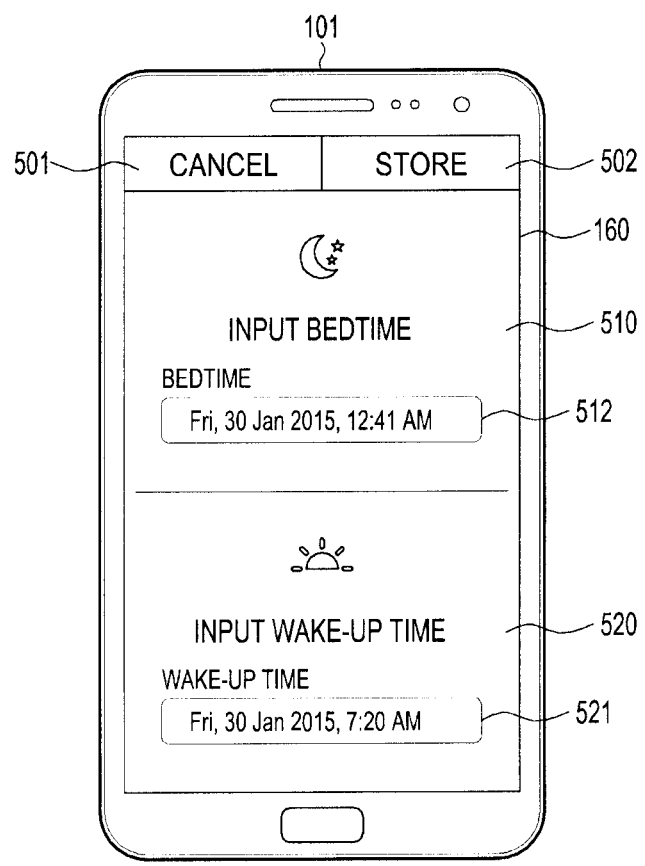
FIG. 5D is a diagram of an example of a user interface, according to various embodiments of the present disclosure.

For example, the user may activate the minute-unit object 544, and the electronic device 101 may display the adjusted sleep information 512 as illustrated in FIG. 5C. The electronic device 101 may display an adjusted minute-unit adjustment object 548. In some implementations, the user may activate the storage object 502 (e.g., a button or another type of input component) so as to save the adjusted sleep information 512. When the storage object 502 is activated (e.g., pressed or touched), the electronic device 101 may store the currently displayed sleep information as sleep information corresponding to the input target date. As illustrated in FIG. 5D, the electronic device 101 may store the adjusted sleep information 512 in the memory of the electronic device 101. Accordingly, the electronic device 101 may store the bedtime on Friday, Jan. 30, 2015 as 12:41 AM, and the wake-up time as 7:20 AM.

Figures 5E, 5F:
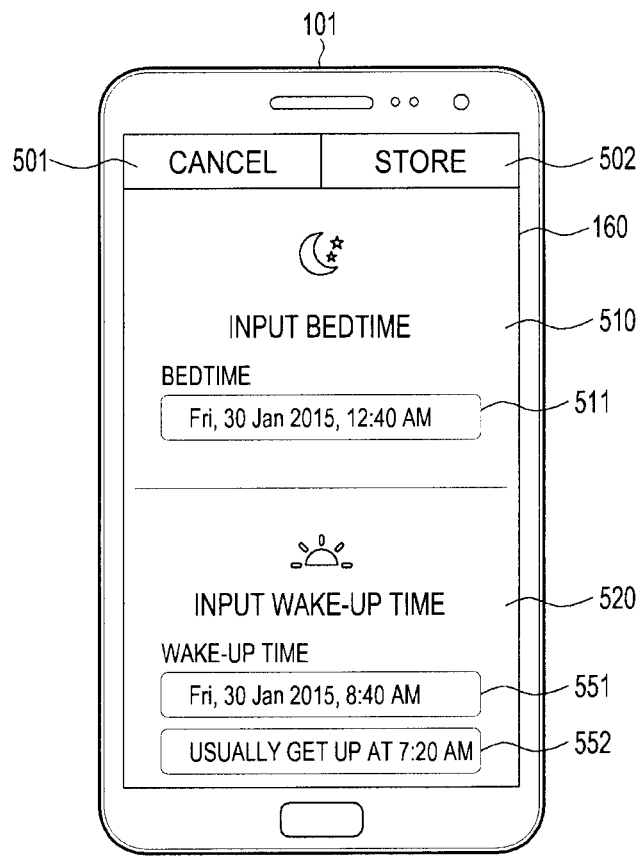
FIG. 5E is a diagram of an example of a data structure, according to various embodiments of the present disclosure.
FIG. 5F is a diagram of an example of a user interface, according to various embodiments of the present disclosure.

FIG. 5E is an example of a data structure containing the stored sleep information according to various embodiments of the present disclosure.

As illustrated in FIG. 5E, the sleep information may contain various sleep information items, such as at least one of a date 550, a bedtime 560, a wake-up time 570, and a sleeping time 580. For example, the electronic device 101 may store a bedtime 562 of 12:41 AM, a wake-up time 572 of 7:20 AM, and a sleeping time 582 of 6 hours and 39 minutes corresponding to a date 552 of January 30. In the meantime, the electronic device 101 may store a bedtime 561 of 12:40 AM, a wake-up time 571 of 7:20 AM, and a sleeping time 581 of 6 hours and 40 minutes corresponding to a date 551 of January 29. In one embodiment, the electronic device 101 may determine a sleep pattern according to the finally stored sleep information. For example, the electronic device 101 may display the sleep information of the date 551 of January 29 as a sleep pattern as illustrated in FIG. 5A. In the meantime, in this case, the electronic device 101 may insert the sleep information of the date 552 of January 30 into the sleep information input screen corresponding to January 31 as the sleep pattern.

Figure 5G:
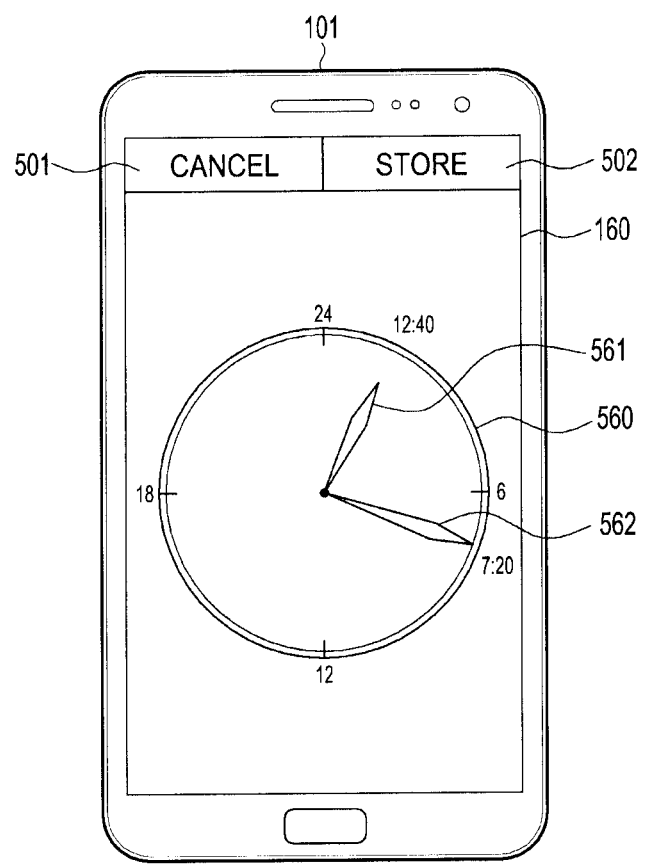
FIG. 5G is a diagram of an example of a user interface, according to various embodiments of the present disclosure.
Figure 5H:
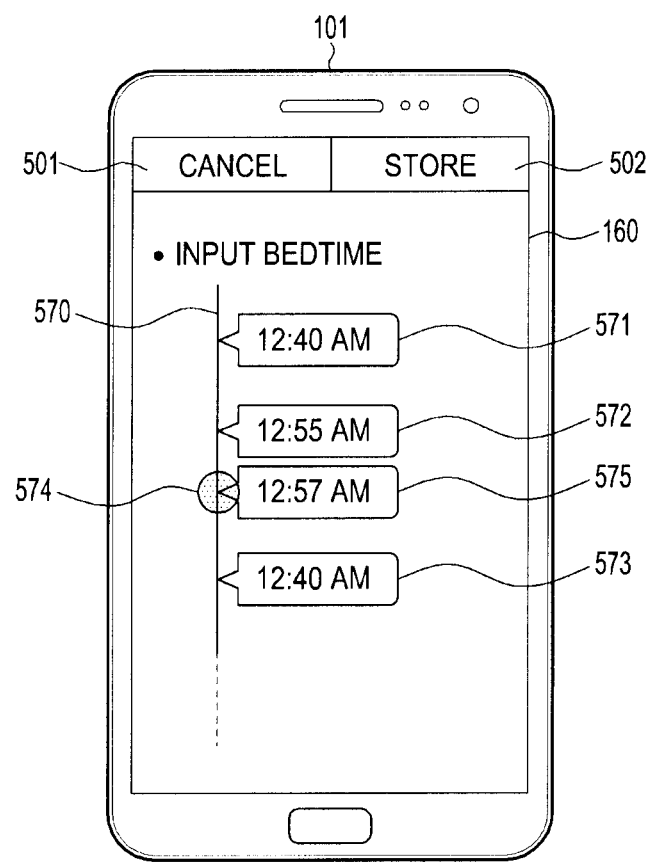
FIG. 5H is a diagram of an example of a user interface, according to various embodiments of the present disclosure.

FIGS. 5F to 5H are diagrams illustrating an example of a sleep information input screen according to various embodiments of the present disclosure.

Referring to FIG. 5F, the electronic device 101 may separate sleep information 552 from a sleep information input window 551 and display the sleep information 552. For example, the electronic device 101 may display a current time as an initial value of the sleep information input window 551. In the meantime, the electronic device 101 may display the sleep information 552 which indicates a particular sleep pattern.

Referring to FIG. 5G, the electronic device 101 according to various embodiments of the present disclosure may also display a sleep information input component 560 having the form of an analog watch. For example, the sleep information input component 560 may include a bedtime display object 561 and a wake-up time display object 562. Here, the electronic device 101 may store a time corresponding to the bedtime display object 561 as a bedtime and a time corresponding to the wake-up time display object 562 as a wake-up time, thereby obtaining and storing sleep information. In the meantime, the electronic device 101 may determine the initial positions of the bedtime display object 561 and the wake-up time display object 562 based on a sleep pattern associated with the user (e.g., a pre-stored sleep pattern). For example, the electronic device 101 may store the sleep pattern including a bedtime of 12:40 AM and a wake-up time of 7:20 AM. Accordingly, the electronic device 101 may locate the bedtime display object 561 at 12:40 AM and the wake-up time display object 562 at 7:20 AM. The user may input sleep information into the sleep information input component 560. For example, the user may drag the bedtime display object 561 and the wake-up time display object 562, and the electronic device 101 may change the time indicated by the bedtime display object 561 and the wake-up time display object 562 in response to the dragging. The electronic device 101 may receive an input of the sleep information as described above. Otherwise, the electronic device 101 may also receive an input of the times corresponding to the initial positions of the bedtime display object 561 and the wake-up time display object 562 as sleep information.

Referring to FIG. 5H, the electronic device 101 according to various embodiments of the present disclosure may display a plurality of sleep information item 571, 572, and 573. For example, the electronic device 101 may store a plurality of sleep patterns. For example, the electronic device 101 may determine a first sleep pattern by using stored sleep information, determine a second sleep pattern by using sensed data, and determine a third sleep pattern by using location information. The electronic device 101 may display the first sleep information item 571 corresponding to the first sleep pattern, the second sleep information item 572 corresponding to the second sleep pattern, and the third sleep information item 573 corresponding to the third sleep pattern. The electronic device 101 may arrange and display the sleep information 571, 572, and 573 on a timetable 570 in time order. The user may designate one point 574 in the timetable, and the electronic device 101 may store a time 575 corresponding to the designated time 574 as sleep information. The electronic device 101 may also display the time 575 corresponding to the designated time 574. Otherwise, the user may also designate one of the currently displayed sleep information 571, 572, and 573 item, and in this case, the electronic device 101 may store the designated sleep information item as the sleep information.

Figure 6:
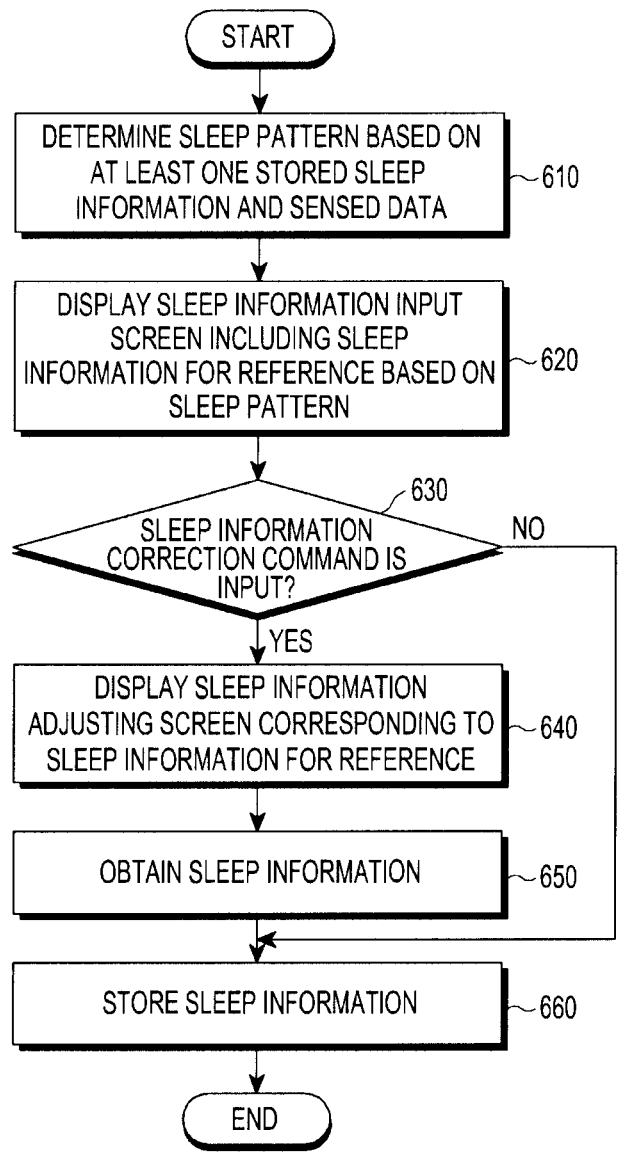
FIG. 6 is a flowchart of an example of a process, according to various embodiments of the present disclosure.

FIG. 6 is a flowchart of an example of a process, according to various embodiments of the present disclosure.

In operation 610, the electronic device 101 may determine a sleep pattern based on at least one of stored sleep information and sensed data. In one embodiment, the electronic device 101 may determine a bedtime and a wake-up time based on the stored sleep information and determine a bedtime and a wake-up time based on the sensed data. The electronic device 101 may also determine a bedtime and a wake-up time based on weighted averages of sleep information determined based on the stored sleep information and sleep information determined based on the sensed data.

In operation 620, the electronic device 101 may display a sleep information input screen containing sleep information based on a sleep pattern. In one embodiment, the electronic device 101 may display the sleep information input screen including a wake-up time and a bedtime. As described above, the sleep information input screen may include an interface capable of inputting a bedtime and a wake-up time, and the bedtime may be set as an initial value of a bedtime input interface and the wake-up time may be set as an initial value of a wake-up time input interface.

In operation 630, the electronic device 101 may determine whether a sleep information correction command is input. The sleep information correction command may be a command for changing the sleep information to another sleep information. When it is determined that the sleep information correction command is input, the electronic device 101 may display a sleep information adjustment screen corresponding to the sleep information in operation 640. The sleep information adjustment screen may be implemented by an interface, through which the sleep information may be changed to another sleep information. In operation 650, the electronic device 101 may obtain sleep information. In operation 660, the electronic device 101 may store the obtained sleep information. In the meantime, when the sleep information correction command is not input, the electronic device 101 may store the sleep information corresponding to the sleep pattern as sleep information.

Figure 7:
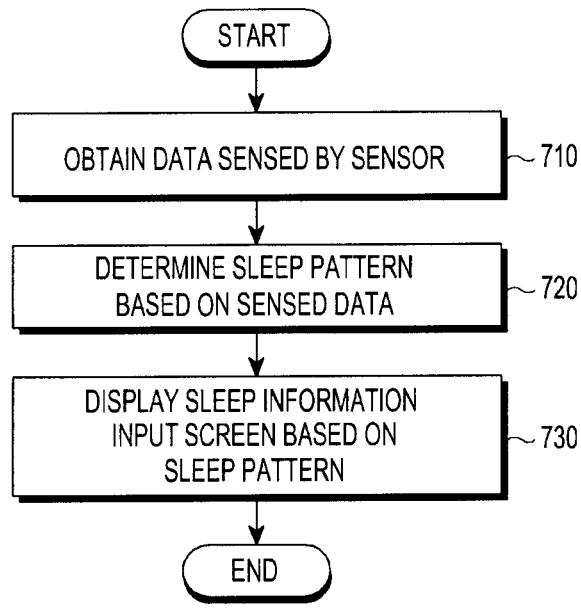
FIG. 7 is a flowchart of an example of a process, according to various embodiments of the present disclosure.

FIG. 7 is a flowchart of an example of a process, according to various embodiments of the present disclosure.

In operation 710, the electronic device 101 may obtain data sensed by a sensor. For example, the electronic device 101 may include a sensor. The electronic device 101 may obtain data sensed by the included sensor. Otherwise, the electronic device 101 may establish communication with an external sensor, and obtain data sensed by the external sensor through communication.

In operation 720, the electronic device 101 may determine a sleep pattern based on the sensed data. In operation 730, the electronic device 101 may display a sleep information input screen determined based on a sleep pattern.

In one embodiment, the electronic device 101 may obtain step counter information from a step counter. The electronic device 101 may determine a sleep pattern by using the step counter information. For example, when a step count per unit time is less than a preset threshold value, the electronic device 101 may determine that a user is in a sleeping state. The electronic device 101 may identify the time at which the user entered the sleeping state as a bedtime and the time at which the user exited the sleeping state as a wake-up time.

In one embodiment, the electronic device 101 may determine the sleep pattern based on sensed data from a motion sensor, such as a 3-axes acceleration sensor, a gyro sensor, and a geomagnetic field sensor. For example, when the degree of movement per unit time is less than a preset threshold value, the electronic device 101 may determine that a user is in a sleeping state. The electronic device 101 may identify the time at which the degree of movement falls below the threshold value as a bedtime and the time at which the degree of movement rises above the threshold value as a wake-up time.

In one embodiment, the electronic device 101 may obtain skin hydration information from a Galvanic Skin Response (GSR) sensor. The electronic device 101 may determine the sleeping state based on the skin hydration information. For example, when the skin hydration belongs to a specific range, the electronic device 101 may determine that the user is in a sleeping state. The electronic device 101 may identify the time at which the user's skin hydration enters the range as a bedtime and the time at which the user's skin hydration exits the range as a wake-up time.

In one embodiment, the electronic device 101 may obtain bio-signal information containing at least one of blood pressure information, HR information, EEG information, ECG information, EMG information, and EOG information from an electrode sensor. The electronic device 101 may determine the sleeping state based on the bio-signal information. For example, when the bio-signal belongs to a specific range, the electronic device 101 may determine that the user is in the sleeping state. The electronic device 101 may identify the time at which the user's bio-signal information enters the range as a bedtime and the time at which the user's bio-signal information exits the range as a wake-up time. In one embodiment, the electronic device 101 may obtain body temperature information from a temperature sensor. The electronic device 101 may determine the sleeping state based on the body temperature information. For example, when a body temperature belongs to a specific range, the electronic device 101 may determine that the user is in the sleeping state. The electronic device 101 may identify the time at which the user's body temperature enters the range as a bedtime and the time at which the user's body temperature exits the range as a wake-up time. In one embodiment, the electronic device 101 may obtain noise information from a sound sensor. The electronic device 101 may determine the sleeping state based on the noise information. For example, when noise belongs to a specific range, the electronic device 101 may determine that the user is in the sleeping state. The electronic device 101 may identify the time at which the user's noise information enters the range as a bedtime and the time at which the user's noise information exits the range as a wake-up time.

As described above, in various embodiments of the present disclosure, the electronic device 101 may determine the sleep pattern by using various sensed data and provide the determined sleep pattern as the sleep information for reference. Accordingly, the user may input sleep information further according to an actual case. More particularly, the user may have difficulty in accurately recognizing a bedtime, and in this case, the user may more accurately input the bedtime based on the sleep information for reference for the sleep pattern provided by the electronic device 101.

Figure 8:
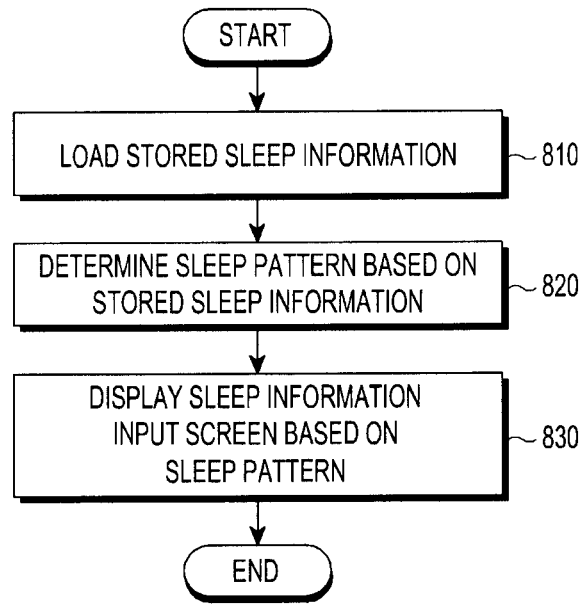
FIG. 8 is a flowchart of an example of a process, according to various embodiments of the present disclosure.

FIG. 8 is a flowchart of an example of a process, according to various embodiments of the present disclosure.

In operation 810, the electronic device 101 may load stored sleep information. For example, the electronic device 101 may pre-store sleep information for each of one or more dates. In order to determine a user's sleep pattern, the electronic device 101 may load the pre-stored sleep information. The electronic device 101 may load sleep information of various periods according to various embodiments of the present disclosure. For example, when the electronic device 101 determines a sleep pattern based on a finally stored sleep information, the electronic device 101 may load only the finally stored sleep information. As another example, when the electronic device 101 determines a sleep pattern based on sleep information for a predetermined period, the electronic device 101 may also load sleep information for the corresponding period.

In operation 820, the electronic device 101 may determine a sleep pattern based on the stored sleep information. In operation 830, the electronic device 101 may display a sleep information input screen determined based on the sleep pattern.

Figure 9A:
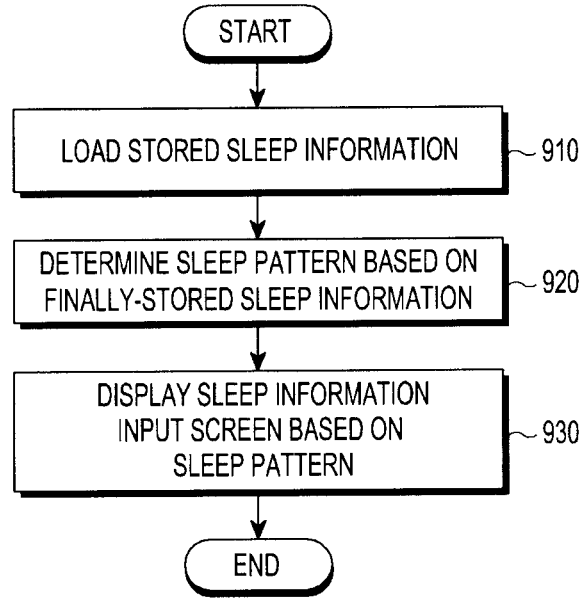
FIG. 9A is a flowchart of an example of a process, according to various embodiments of the present disclosure.
Figure 9B:
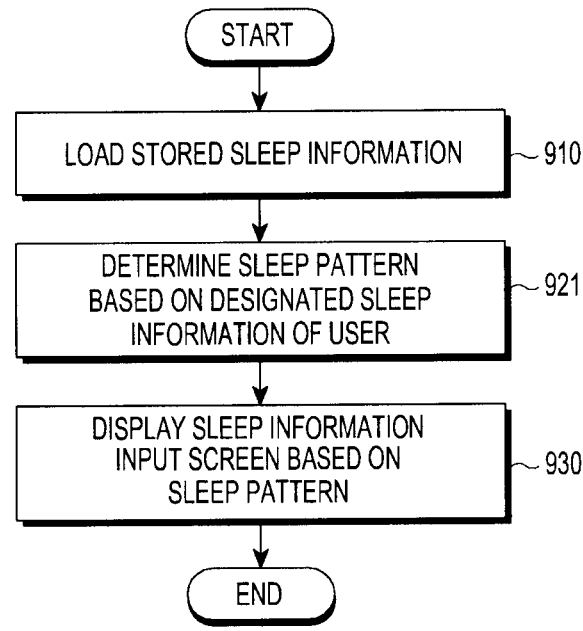
FIG. 9B is a flowchart of an example of a process, according to various embodiments of the present disclosure.
Figure 9C:
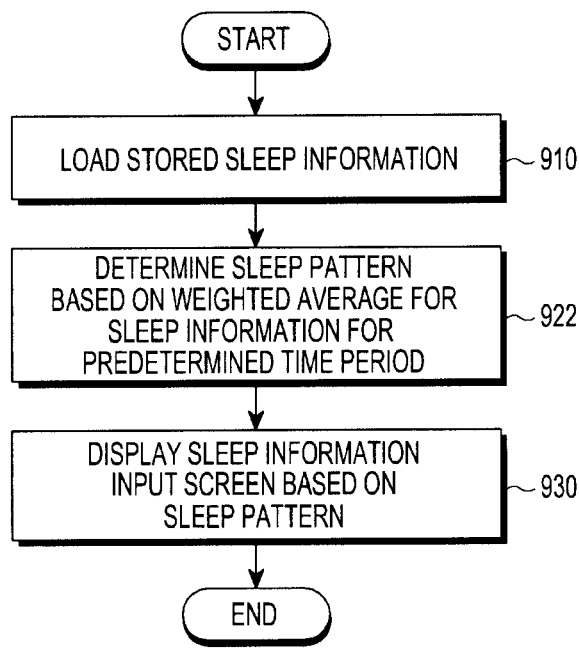
FIG. 9C is a flowchart of an example of a process, according to various embodiments of the present disclosure.

FIGS. 9A to 9C are flowcharts of examples of different processes, according to various embodiments of the present disclosure.

In operation 910, the electronic device 101 may load stored sleep information. In operation 920, the electronic device 101 may determine a sleep pattern based on finally stored sleep information. In this case, in operation 910, the electronic device 101 may also load only the finally stored sleep information. The electronic device 101 may determine a sleep pattern including at least one of a bedtime and a wake-up time of the finally stored sleep information. In operation 930, the electronic device 101 may display a sleep information input screen determined based on the sleep pattern. For example, the electronic device 101 may display a bedtime associated with the sleep pattern as a bedtime for reference, and a wake-up time associated with the sleep pattern as a wake-up time for reference.

In the meantime, the electronic device 101 according to various embodiments of the present disclosure may manage the finally stored sleep information by various schemes. In one embodiment, the electronic device 101 may manage the finally stored sleep information as sleep information corresponding to a date just before an input target date. In another embodiment, the electronic device 101 may also separate and manage sleep information of weekdays and sleep information of a weekend. In such instances, the finally stored sleep information for the weekend may also include sleep information corresponding to a weekend just before an input target date. In another embodiment, the electronic device 101 may also separate and manage sleep information based on the type of day the sleep information is associated with (e.g., holiday or business day). In such instances, the finally stored sleep information for the business day or the holiday may also include sleep information corresponding to a business day or a holiday just before an input target date. In another embodiment, the electronic device 101 may also manage sleep information for specific locations. In this case, the finally stored sleep information for the first location may be sleep information finally stored at the first place.

FIG. 9B is a flowchart illustrating a process for controlling the electronic device according to various embodiments of the present disclosure. In FIG. 9B, unlike FIG. 9A, in operation 921, the electronic device 101 may determine a sleep pattern based on sleep information designated by a user. For example, the user may designate sleep information corresponding to a specific date in stored sleep information. In this case, the electronic device 101 may manage sleep information corresponding to the designated date as a sleep pattern. In another embodiment, the user may also directly input a sleep pattern, and the electronic device 101 may also manage the directly input sleep pattern.

FIG. 9C is a flowchart illustrating an example of a process for controlling the electronic device according to various embodiments of the present disclosure. In FIG. 9C, unlike FIG. 9A, in operation 922, the electronic device 101 may also determine a sleep pattern based on a weighted average for sleep information during a predetermined period. For example, the electronic device 101 may determine a sleep pattern based on Equation 1.

$$d_m = w_{m-1}(s_{m-1} - g_{m-1}) + w_{m-2}(s_{m-2} - g_{m-1}) + w_{m-1} + (s_{m-3} - g_{m-1}) + w_{m-4} + (s_{m-4} - g_{m-1}) + w_{m-5} + (s_{m-5} - g_{m-1})$$

Equation 1

Equation 1 relates to a case where the predetermined period is set to five days, and $g_{m-i}$ may be an average sleep or a wake-up time at the m-$i^{th}$ date, $s_{m-i}$ may be a sleeping or wake-up time at the m-$i^{th}$ date, $w_{m-i}$ is a weighted value at the m-$i^{th}$ date, a sum of $w_i$ may be 1, and $d_m$ is a difference between the $m^{th}$ average sleep or wake-up time ($g_m$) and the m-$i^{th}$ average sleep or wake-up time ($g_{m-i}$). In the meantime, an average sleep or a wake-up time $g_m$ provided at the $m^{th}$ date is $g_{m-i} + d_m$. The electronic device 101 may determine the weighted average $g_m$ determined as described above as a sleep pattern.

Figure 10:
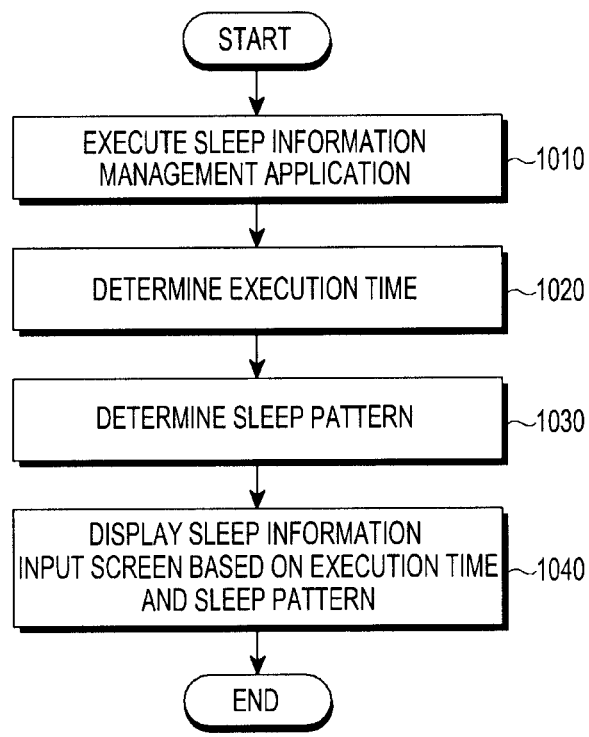
FIG. 10 is a flowchart of an example of a process, according to various embodiments of the present disclosure.

FIG. 10 is a flowchart illustrating an example of a process for controlling the electronic device according to various embodiments of the present disclosure.

In operation 1010, the electronic device 101 may execute a sleep information management application. As described above, the sleep information management application may be an application capable of establishing a sleep information database by receiving sleep information. The sleep information management application may configure and display a sleep information input screen, and for example, configure the sleep information input screen according to a sleep pattern.

In the meantime, the electronic device 101 may display a menu screen including an execution icon of one or more applications. The electronic device 101 may also display an execution icon for the sleep information management application, and a user may designate an execution icon for the sleep information management application for executing the sleep information management application. The electronic device 101 may execute the sleep information management application based on an execution command, such as designating the execution icon.

In operation 1020, the electronic device 101 may determine an execution time of the sleep information management application. For example, the electronic device 101 may determine a current time based on an internal clock or data received from another device, and determine the execution time based on a current time at a time, at which the execution command of the sleep information management application is input.

In operation 1030, the electronic device 101 may determine a sleep pattern. As described above, the electronic device 101 may determine a sleep pattern according to various types of information, such as sensed data, stored sleep information, location information, an execution time, information of another electronic device, and use information of the electronic device 101.

In operation 1040, the electronic device 101 may display the sleep information input screen based on the execution time and the sleep pattern. For example, the electronic device 101 may determine an input target date by comparing the determined sleep pattern and the execution time. Otherwise, the electronic device 101 may also determine sleep information for reference by comparing the determined sleep pattern and the execution time. This will be described in detail below.

Figure 11:
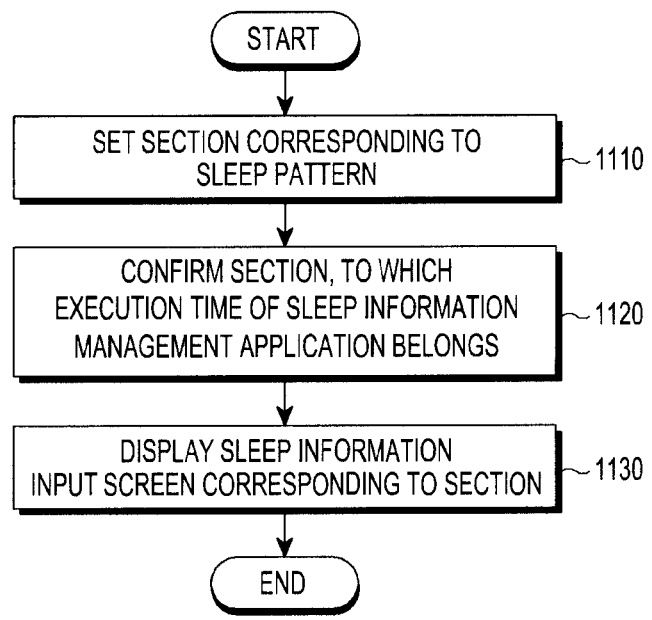
FIG. 11 is a flowchart of an example of a process, according to various embodiments of the present disclosure.
Figure 12:
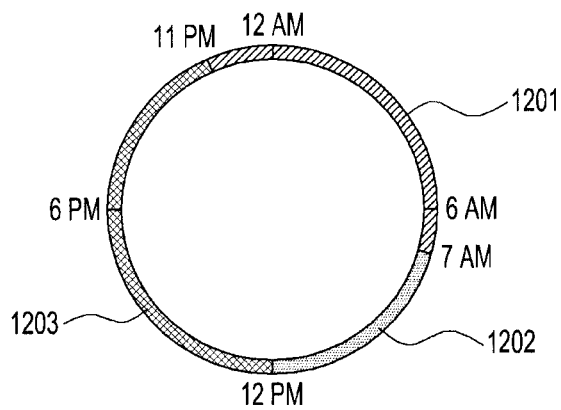
FIG. 12 is a diagram illustrating an example of setting a section according to a sleep pattern according to various embodiments of the present disclosure.
Figure 13A:
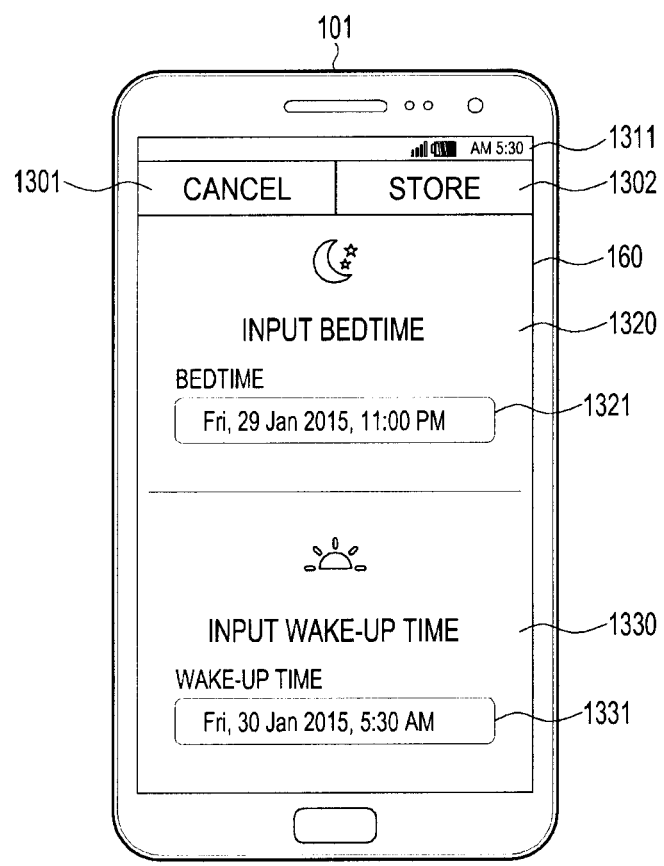
FIG. 13A is a diagram of an example of a user interface, according to various embodiments of the present disclosure.
Figure 13B:
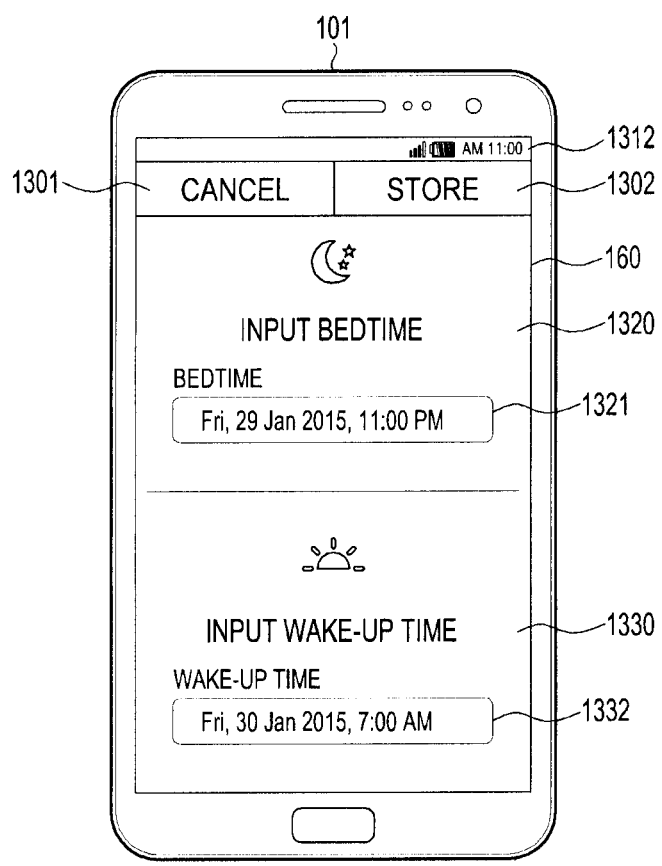
FIG. 13B is a diagram of an example of a user interface, according to various embodiments of the present disclosure.
Figure 13C:
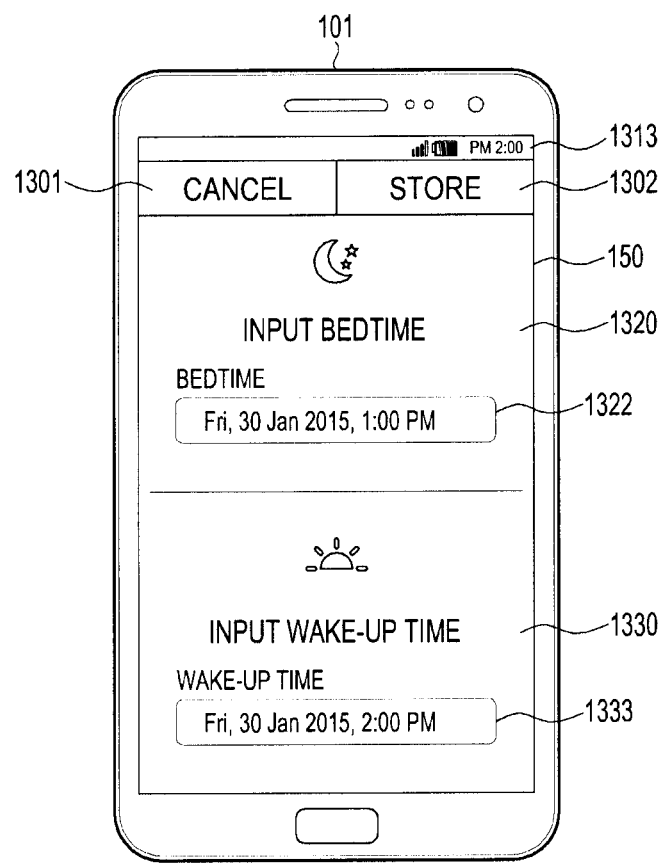
FIG. 13C is a diagram of an example of a user interface, according to various embodiments of the present disclosure.

FIG. 11 is a flowchart illustrating a process for displaying a sleep information input screen according to various embodiments of the present disclosure. The process of FIG. 11 will be described in more detail with reference to FIGS. 12, and 13A to 13C. FIG. 12 is a diagram illustrating an example of setting a section according to a sleep pattern according to various embodiments of the present disclosure. FIGS. 13A to 13C are diagrams illustrating an example of a sleep information input screen according to various embodiments of the present disclosure.

In operation 1110, the electronic device 101 may set a section in response to a sleep pattern. For example, the electronic device 101 may store a sleep pattern that a user goes to sleep at 11:00 PM, and wakes up at 7:00 AM. The electronic device 101 may set a sleeping section 1201 in response to the sleep pattern as illustrated in FIG. 12. As illustrated in FIG. 12, the sleeping section 1201 may be set from 11:00 PM to 7:00 AM. The electronic device 101 may set a morning section 1202 from the wake-up time of 7:00 AM to noon. The electronic device 101 may set an afternoon section 1203 from noon to the bedtime time of 11:00 PM to noon. In the meantime, in various embodiments of the present disclosure, the electronic device 101 may also set a section as a sleeping section and a non-sleeping section. In another embodiment, the electronic device 101 may further segmentalized a section and further set an additional sleeping section, such as a nap section. In the meantime, setting noon to a boundary of the morning section 1202 and the afternoon section 1203 is simply for illustrative purposes, and the electronic device 101 may also set another time as a boundary of the morning section 1202 and the afternoon section 1203.

In operation 1120, the electronic device 101 may identify a section, to which an execution time of a sleep information management application belongs. In operation 1130, the electronic device 101 may display a sleep information input screen corresponding to the confirmed section.

For example, as illustrated in FIG. 13A, the electronic device 101 may detect that the section, to which the execution time of the sleep information management application belongs, is a sleeping section. As illustrated in FIG. 13A, the electronic device 101 may confirm that the current time 1311 is 5:30 AM. Further, it is assumed that the sleep information management application is executed at 5:30 AM. As described above, in the present embodiment, the sleeping section 1201 is set from 11:00 PM to 7:00 AM, so that the electronic device 101 may confirm that the section, to which the execution time of a sleep information management application belongs, is the sleeping section 1201.

The electronic device 101 may display the sleep information input screen determined based on the sleep pattern and the execution time. The electronic device 101 may display a cancel object 1301, a storage object 1302, a sleep information input screen 1320, and a wake-up information input screen 1330. The electronic device 101 may display a sleep information input window 1321 and a wake-up information input window 1331. The electronic device 101 may display 11:00 PM, which is a bedtime for reference by the sleep pattern as an initial value of the sleep information input window 1321. The electronic device 101 may display 5:30 PM that is the execution time of the sleep information management application as an initial value of the wake-up information input window 1331. The execution of the sleep information management application may be determined as the user wakes up so that the electronic device 101 may display the execution time of the sleep information management application, not the wake-up time for reference by the sleep pattern, as the initial value of the wake-up information input window 1331.

In the meantime, in another example, as illustrated in FIG. 13B, the electronic device 101 may determine the execution time of the sleep information management application as 11:00 AM like the current time 1312. As described above, in the present embodiment, the morning section 1202 is set from 7:00 AM to noon, so that the electronic device 101 may detect that the section, to which the execution time of a sleep information management application belongs, is the morning section 1202.

The electronic device 101 may display the sleep information input screen determined based on the sleep pattern and the execution time. The electronic device 101 may display 11:00 PM, which is a bedtime for reference by the sleep pattern as an initial value of the sleep information input window 1321. The electronic device 101 may display 7:00 AM, which is a wake-up time for reference by the sleep pattern as an initial value of the sleep information input window 1331. As described above, it may be determined that the execution of the sleep information management application means the wake-up of the user, so that the electronic device 101 may determine that the user wakes up after the wake-up time by the sleep pattern. Accordingly, the electronic device 101 may display the wake-up time for reference by the sleep pattern as an initial value of the wake-up information input window 1331.

As another example, as illustrated in FIG. 13C, the electronic device 101 may determine the execution time of the sleep information management application as 2:00 PM like a current time 1313. As described above, in the present embodiment, the afternoon section 1203 is set from noon to 11:00 PM, so that the electronic device 101 may detect that the section, to which the execution time of a sleep information management application belongs, is the afternoon section 1203.

The electronic device 101 may display the sleep information input screen determined based on the sleep pattern and the execution time. The electronic device 101 may use sleep pattern information for a nap as an initial value of the bedtime information input window 1322. For example, the electronic device 101 may also further store a nap section from 2:00 PM to 3:00 PM as the sleep pattern. The electronic device 101 may display 2:00 PM, which is a bedtime for reference by the sleep pattern. The electronic device 101 may display 3:00 PM, which is a wake-up time for reference by the sleep pattern or 3:00 PM by an execution time of an application as an initial value of a wake-up information input window 1333.

Figure 14:
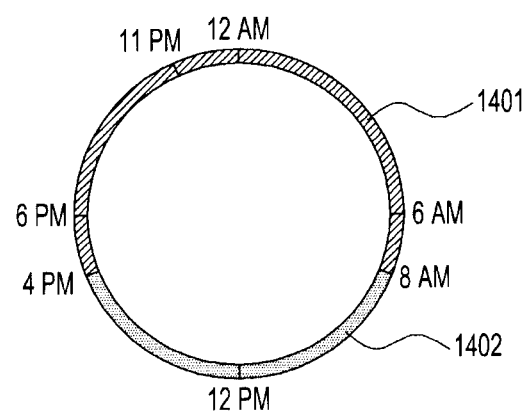
FIG. 14 is a diagram illustrating an example of setting a section according to a sleep pattern according to another embodiment of the present disclosure.
Figure 15A:
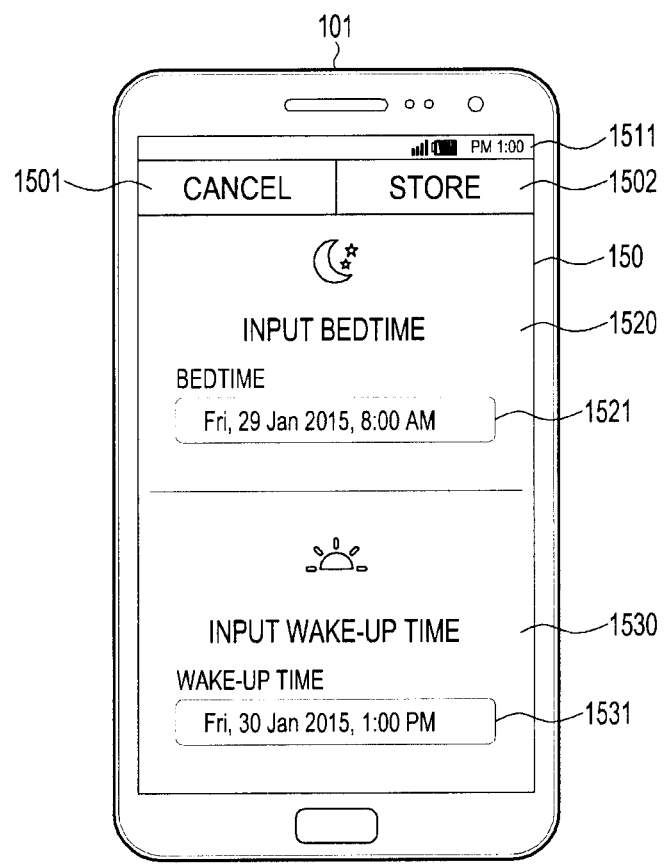
FIG. 15A is a diagram of an example of a user interface, according to various embodiments of the present disclosure.
Figure 15B:
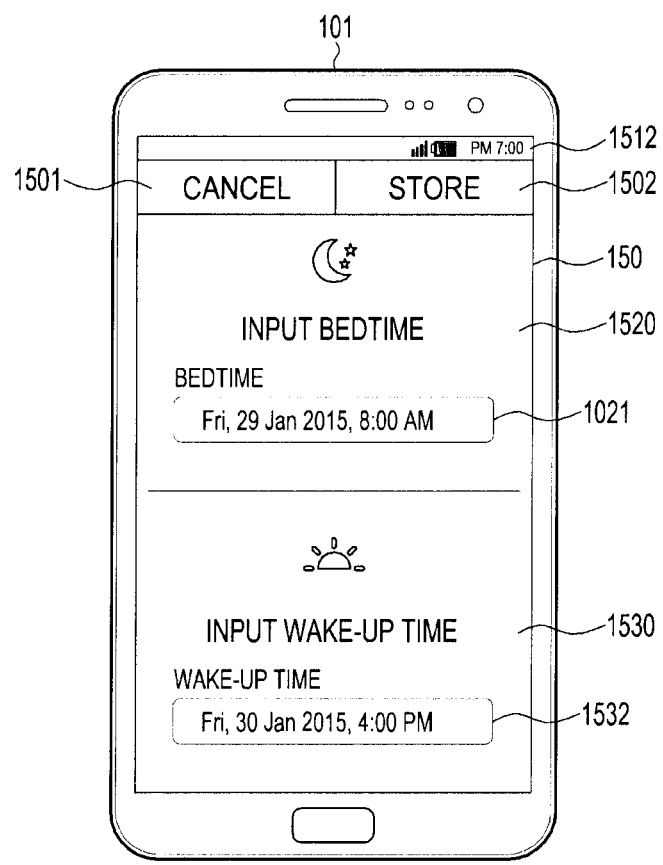
FIG. 15B is a diagram of an example of a user interface, according to various embodiments of the present disclosure.

FIG. 14 is a diagram illustrating an example of a process for setting a section according to a sleep pattern according to another embodiment of the present disclosure. FIGS. 15A and 15B are diagrams illustrating an example of the sleep information input screen according to various embodiments of the present disclosure.

As described above, the electronic device 101 may set a section in response to a sleep pattern. For example, the electronic device 101 may store a sleep pattern that a user goes to sleep at 8:00 AM, and wakes up at 4:00 PM. When the user is a nighttime worker, the electronic device 101 may also store the aforementioned sleep pattern.

The electronic device 101 may set a sleeping section 1401 in response to the sleep pattern as illustrated in FIG. 14. As illustrated in FIG. 14, the sleeping section 1401 may be set from 8:00 AM to 4:00 PM. The electronic device 101 may set a non-sleeping section 1402 from the wake-up time of 4:00 PM to 8:00 AM that is the bedtime. When the sleeping section 1401 includes noon as illustrated in FIG. 14, the electronic device 101 may set the section as the sleeping section 1401 and the non-sleeping section 1402.

The electronic device 101 may identify a section, to which an execution time of a sleep information management application belongs. The electronic device 101 may display the sleep information input screen corresponding to the identified section.

For example, as illustrated in FIG. 15A, the electronic device 101 may detect that the section, to which the execution time of the sleep information management application belongs, is the sleeping section. As illustrated in FIG. 15A, the electronic device 101 may detect that the current time 1511 is 1:00 PM. Further, it is assumed that the sleep information management application is executed at 1:00 PM. As described above, in the present embodiment, since the sleeping section 1401 is set from 8:00 AM to 4:00 PM, the electronic device 101 may detect that the section, to which the execution time of the sleep information management application belongs, is the sleeping section 1401.

The electronic device 101 may display the sleep information input screen determined based on the sleep pattern and the execution time. The electronic device 101 may display a cancel object 1501, a storage object 1502, a sleep information input screen 1520, and a wake-up information input screen 1530. The electronic device 101 may display a sleep information input window 1521 and a wake-up information input window 1531. The electronic device 101 may display 8:00 AM, which is a bedtime for reference by the sleep pattern as an initial value of the sleep information input window 1521. The electronic device 101 may display 1:00 PM that is the execution time of the sleep information management application as an initial value of the wake-up information input window 1531. The execution of the sleep information management application may be determined as the user wakes up so that the electronic device 101 may display the execution time of the sleep information management application, not the wake-up time for reference by the sleep pattern, as the initial value of the wake-up information input window 1531.

As another example, as illustrated in FIG. 15B, the electronic device 101 may determine the execution time of the sleep information management application as 11:00 AM like a current time 1512. As described above, in the present embodiment, since a non-sleeping section 1502 is set from 4:00 PM to 8:00 AM, the electronic device 101 may detect that the section, to which the execution time of the sleep information management application belongs, is the non-sleeping section 1502.

The electronic device 101 may display the sleep information input screen determined based on the sleep pattern and the execution time. The electronic device 101 may display 8:00 AM, which is a bedtime for reference by the sleep pattern as an initial value of the sleep information input window 1521. The electronic device 101 may display 4:00 PM, which is a wake-up time for reference by the sleep pattern as an initial value of the wake-up information input window 1531. As described above, it may be determined that the execution of the sleep information management application means the wake-up of the user, so that the electronic device 101 may determine that the user wakes up after the wake-up time associated with the sleep pattern. Accordingly, the electronic device 101 may display the wake-up time for reference by the sleep pattern as the initial value of the wake-up information input window 1531.

Figure 16:
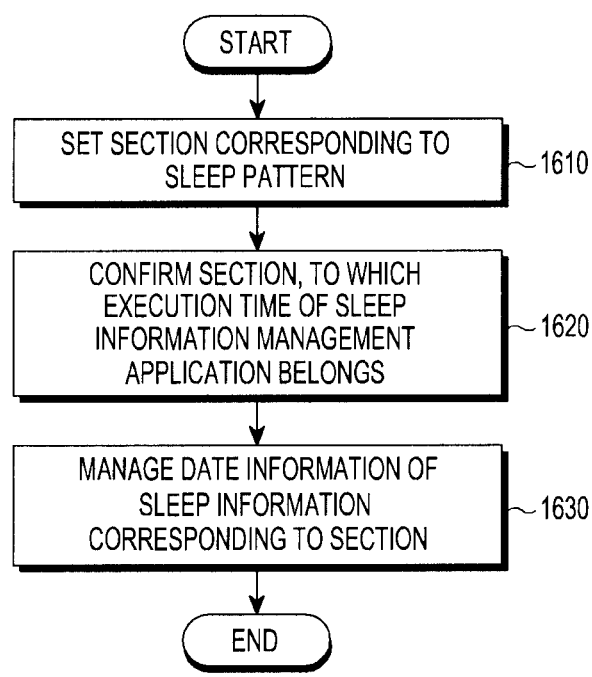
FIG. 16 is a flowchart of an example of a process, according to various embodiments of the present disclosure.
Figure 17A:
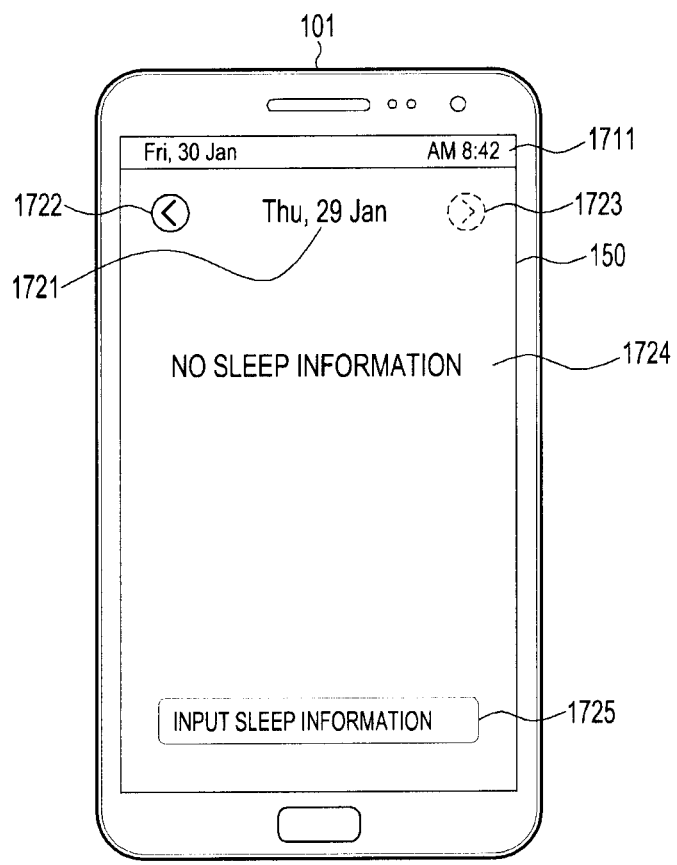
FIG. 17A is a diagram of an example of a user interface, according to various embodiments of the present disclosure.
Figure 17B:
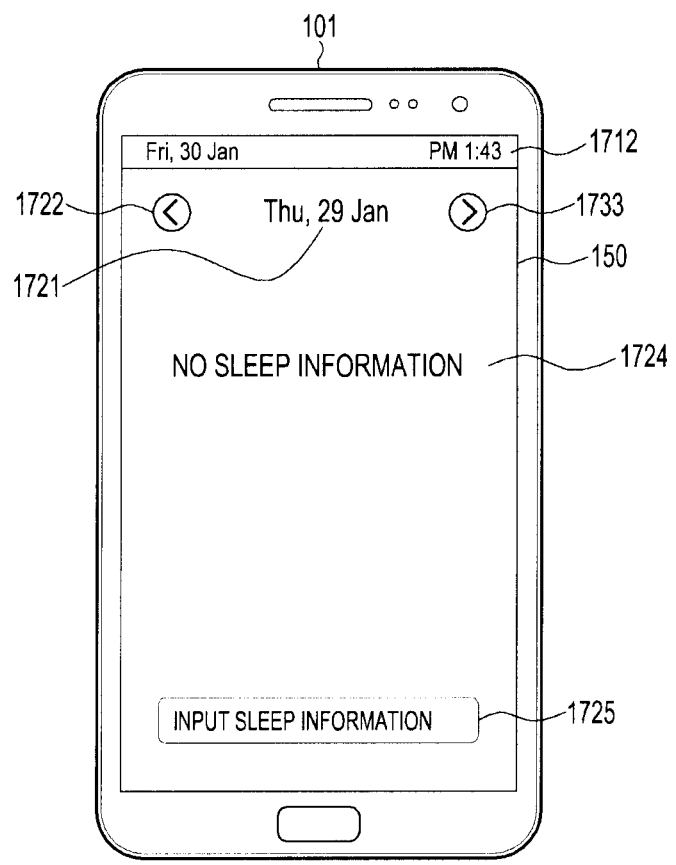
FIG. 17B is a diagram of an example of a user interface, according to various embodiments of the present disclosure.
Figure 17C:
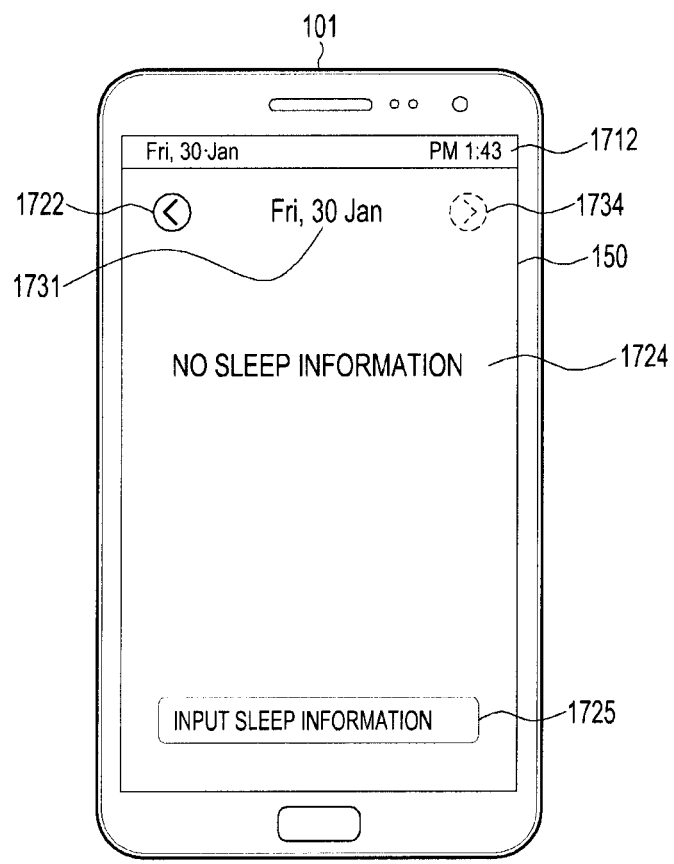
FIG. 17C is a diagram of an example of a user interface, according to various embodiments of the present disclosure.

FIG. 16 is a flowchart illustrating an example of a process for determining an input target date according to various embodiments of the present disclosure. The process of FIG. 16 will be described in more detail with reference to FIGS. 17A to 17C. FIGS. 17A to 17C are diagrams illustrating examples of a sleep information confirmation screen according to various embodiments of the present disclosure.

In operation 1610, the electronic device 101 may set a section in response to a sleep pattern. In one embodiment, the electronic device 101 may set the sleeping section 1201, the morning section 1202, and the afternoon section 1203 as illustrated in FIG. 12.

In operation 1620, the electronic device 101 may identify a section, to which an execution time of a sleep information management application belongs. For example, as illustrated in FIG. 17A, the electronic device 101 may detect that the execution time of the sleep information management application is 8:42 AM on January 30. Further, it can be detected that the execution time of the sleep information management application belongs to the morning section 1202. The electronic device 101 may display a sleep information corresponding to January 29 in response to the detection. The electronic device 101 may receive sleep information corresponding to a date before the corresponding date in response to the sleep information input in the morning section 1202. That is, the electronic device 101 may manage the sleep information input before noon as sleep information corresponding to the previous date based on noon, and the sleep information input after noon may be managed as the sleep information corresponding to a date of a current time.

In various embodiments of the present disclosure, the sleep information confirming screen may display a confirmation target date 1721. For example, in the embodiment of FIG. 17A, the electronic device 101 may display the sleep information confirming screen corresponding to January 29. The sleep information confirming screen may include confirmation target date change objects 1722 and 1723. For example, when the confirmation target date change objects 1722 and 1723 are designated, the electronic device 101 may change the confirmation target date. In the meantime, in the embodiment of FIG. 17A, since the electronic device 101 obtains the sleep information on January 29 as described above, it can be confirmed that the target date change object 1723 to January 30 is not activated.

The sleep information confirming screen may include sleep information 1724. In the embodiment of FIG. 17A, the electronic device 101 may display sleep information corresponding to the confirmation target date 1721. When there is no sleep information, the electronic device 101 may display an indication that there is no sleep information, and when there is the sleep information, the electronic device 101 may display an indication that there is the sleep information. When there is no sleep information, the electronic device 101 may display a sleep information input object 1725. When there is the sleep information, the electronic device 101 may also display a sleep information detail confirming object or a sleep information editing object instead of the sleep information input object 1725. When the sleep information input object 1725 is designated, the electronic device 101 may display a sleep information input screen. Even when the sleep information editing object is displayed, the electronic device 101 may display the sleep information input screen. In some implementations, the sleep information management application may analyze the stored sleep information, and for example, when the sleep information detail confirming object is activated (e.g., touched or pressed), the electronic device 101 may provide a corresponding analysis result. For example, the electronic device 101 may provide the analysis result, such as a sleeping time and sleep efficiency.

FIG. 17B is a flowchart of an example of a process, according to various embodiments of the present disclosure. In the embodiment of FIG. 17B, the electronic device 101 may detect that a current time 1712 that is an execution time of an application is 1:43 PM. Accordingly, the electronic device 101 may receive sleep information corresponding to January 30, and a target date change object 1733 to January 30 may be activated. When the target date change object 1733 is activated, the electronic device 101 may display a sleep information confirming screen corresponding to January 30. FIG. 17C is a diagram illustrating an example of the sleep information confirming screen corresponding to January 30 according to various embodiments of the present disclosure. The electronic device 101 may display the sleep information confirming screen corresponding to January 30 1731. Since the electronic device 101 obtains sleep information corresponding to January 31, a target date change object 1734 to January 31 may be non-activated again.

Figure 18:
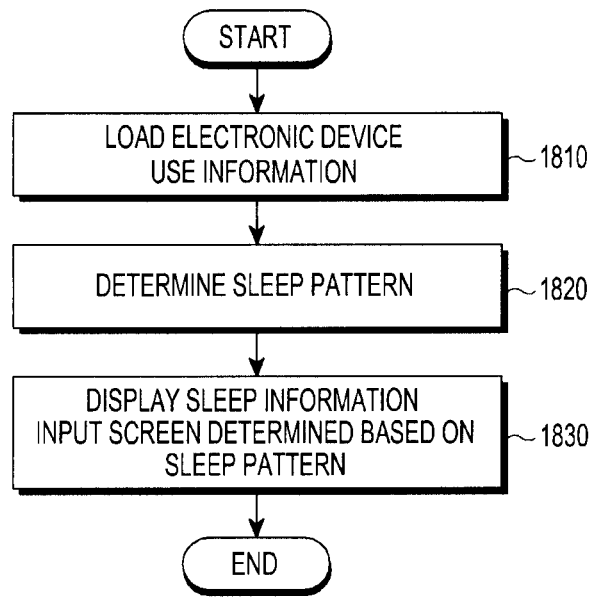
FIG. 18 is a flowchart of an example of a process, according to various embodiments of the present disclosure.

FIG. 18 is a flowchart of an example of a process, according to various embodiments of the present disclosure.

In operation 1810, the electronic device 101 may load use information of the electronic device 101. In operation 1820, the electronic device 101 may determine a sleep pattern based on the loaded use information. In operation 1830, the electronic device 101 may display a sleep information input screen determined based on a sleep pattern.

In one embodiment, the electronic device 101 may determine a sleep pattern based on use information of various applications including a sleep information application. For example, the electronic device 101 may determine a wake-up time of the sleep pattern based on time, at which an execution command for the application is obtained. The electronic device 101 may display the sleep information input screen including the time, at which the execution command for the application is obtained, as a wake-up time for reference.

In one embodiment, the electronic device 101 may obtain a time, at which an alarm application is released, and determine the wake-up time of the sleep pattern based on the obtained time. The electronic device 101 may display the sleep information input screen including the time, at which the alarm application is released, as a wake-up time for reference.

In one embodiment, the electronic device 101 may also determine the sleep pattern according to information input into a schedule management application. For example, the electronic device 101 may confirm a nighttime working date and a daytime working date of a user according to the information described in the schedule management application. Accordingly, the electronic device 101 may select one of a sleep pattern corresponding to nighttime work or a sleep pattern corresponding to daytime work in response to a specific input target date, and display the sleep information input screen determined based on the selected sleep pattern.

In one embodiment, the electronic device 101 may obtain a turn-on time of the display 160 or an unlock time of the electronic device 101, and determine a wake-up time of the sleep pattern based on the obtained time. The electronic device 101 may display the sleep information input screen including the turn-on time of the display 160 or the unlock time of the electronic device 101 as the wake-up time for reference.

In one embodiment, the electronic device 101 may obtain a time, at which the display 160 is turned off, and determine a bedtime of the sleep pattern based on the obtained time. The electronic device 101 may display the sleep information input screen including the time, at which the display 160 is turned off, as the bedtime for reference.

Figure 19:
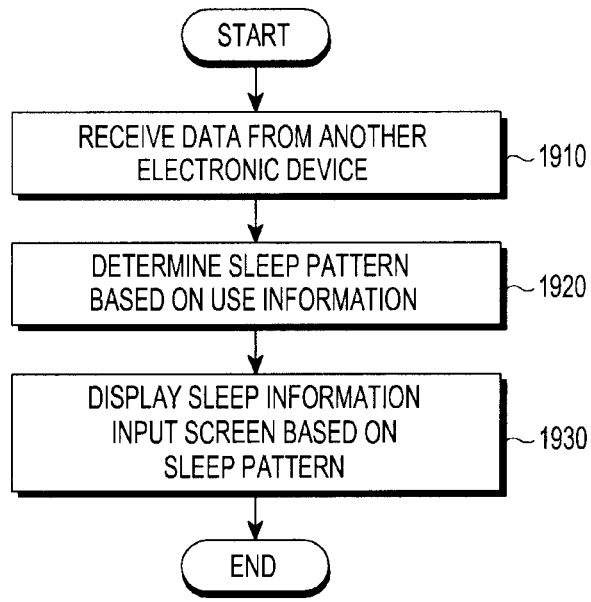
FIG. 19 is a flowchart of an example of a process, according to various embodiments of the present disclosure.
Figure 20:
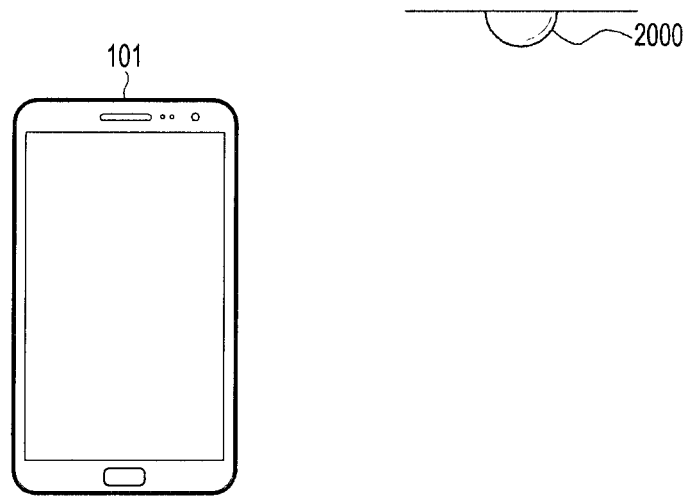
FIG. 20 is a diagram illustrating an example of a process for receiving data from an external device, according to various embodiments of the present disclosure.
Figure 21:
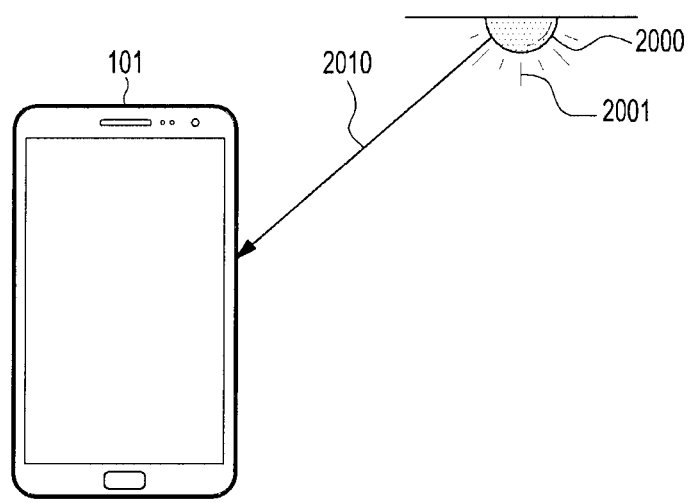
FIG. 21 is a diagram illustrating an example of a process for receiving data from an external device, according to various embodiments of the present disclosure.

FIG. 19 is a flowchart of an example of a process, according to various embodiments of the present disclosure. The process of FIG. 19 will be described in more detail with reference to FIGS. 20 and 21. FIGS. 20 and 21 are diagrams illustrating an example of a process for receiving information from an external device, according to various embodiments of the present disclosure.

In operation 1910, the electronic device 101 may receive data from another electronic device through communication. For example, as illustrated in FIGS. 20 and 21, a state of a lamp 2000 may be changed from a turn-off state to a turn-on state 2001. Further, the lamp 2000 may transmit data 2010 regarding the change in the state of the lamp 2000 to the turn-on state to the electronic device 101. In the meantime, in FIGS. 20 and 21, it is illustrated that the lamp 2000 directly transmits the data 2010 to the electronic device 101, but this is simply for illustrative purposes, a relay device (not illustrated) may also relay the data 2010 to the electronic device 101.

In operation 1920, the electronic device 101 may determine a sleep pattern based on the received data. For example, the electronic device 101 may determine a wake-up time of the sleep pattern based on a turn-on time of the lamp 2000. The electronic device 101 may display a sleep information input screen including the turn-on time of the lamp 2000, as the wake-up time for reference.

In operation 1930, the electronic device 101 may display a sleep information input screen determined based on the sleep pattern.

In the meantime, in various embodiments of the present disclosure, the electronic device 101 may determine the sleep pattern based on data, such as a computer use history, an SNS use history, and a home appliance use history, from various other electronic devices.

Figure 22:
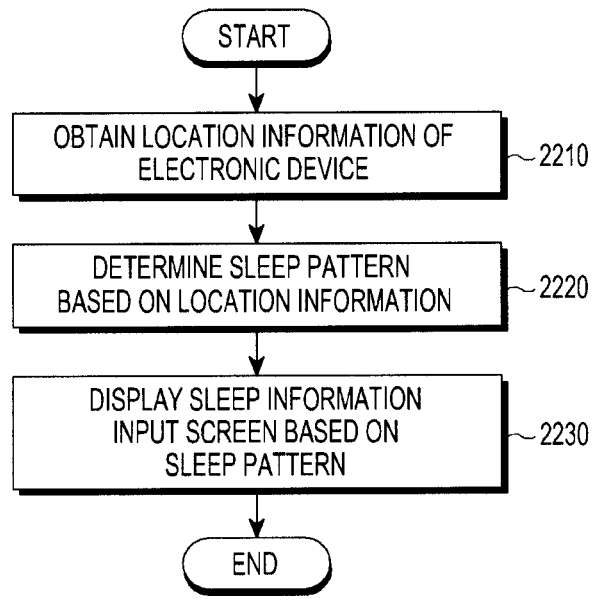
FIG. 22 is a flowchart of an example of a process, according to various embodiments of the present disclosure.

FIG. 22 is a flowchart illustrating a method of controlling an electronic device according to various embodiments of the present disclosure.

In operation 2210, the electronic device 101 may obtain location information of the electronic device 101. For example, the electronic device 101 may obtain location information based on data from a GPS module included therein.

In operation 2220, the electronic device 101 may determine a sleep pattern based on the location information. For example, the electronic device 101 may manage a sleep pattern for each location. For example, the electronic device 101 may manage a first sleep pattern corresponding to home and manage a second sleep pattern corresponding to a dormitory. The electronic device 101 may determine one of the first sleep pattern and the second sleep pattern according to the confirmed location.

In operation 2230, the electronic device 101 may display a sleep information input screen determined based on the sleep pattern.

Figure 23:
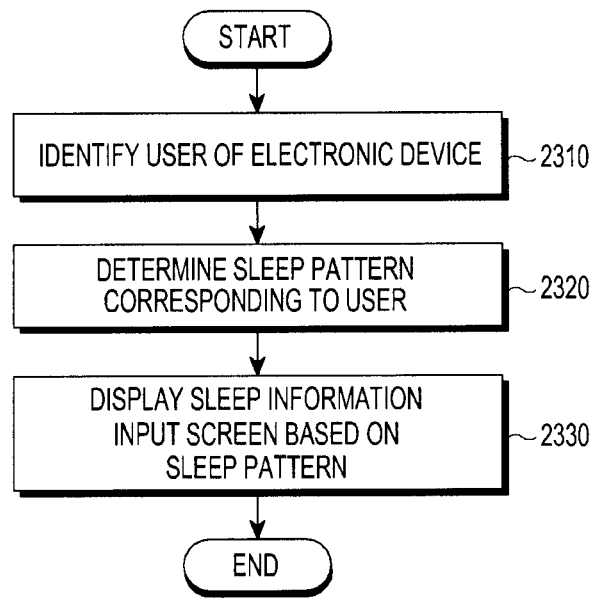
FIG. 23 is a flowchart of an example of a process, according to various embodiments of the present disclosure.

FIG. 23 is a flowchart illustrating a method of controlling the electronic device according to various embodiments of the present disclosure.

In operation 2310, the electronic device 101 may identify a user of the electronic device 101. The electronic device 101 may identify the user, for example, in response to a logged-in user identifier.

In operation 2320, the electronic device 101 may determine a sleep pattern based on the confirmed user. For example, the electronic device 101 may manage a sleep pattern for each user. For example, the electronic device 101 may manage a first sleep pattern corresponding to a first user and manage a second sleep pattern corresponding to a second user. The electronic device 101 may determine one of the first sleep pattern and the second sleep pattern according to the confirmed user.

In operation 2330, the electronic device 101 may display a sleep information input screen determined based on the sleep pattern.

Figure 24:
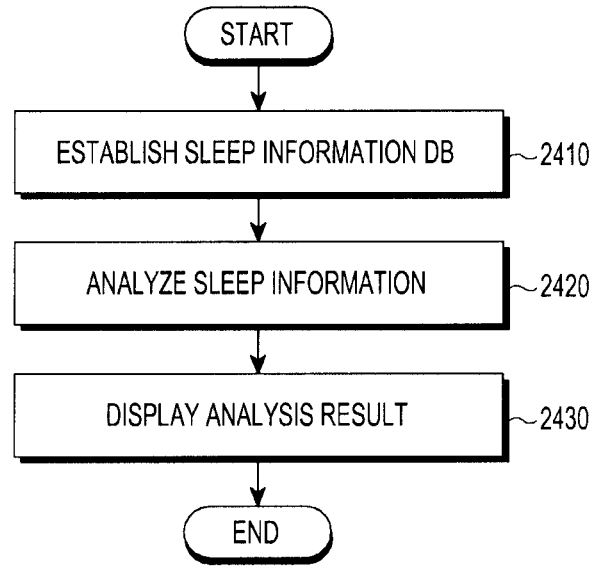
FIG. 24 is a flowchart of an example of a process, according to various embodiments of the present disclosure.

FIG. 24 is a flowchart illustrating a method of controlling an electronic device according to various embodiments of the present disclosure.

Figure 25:
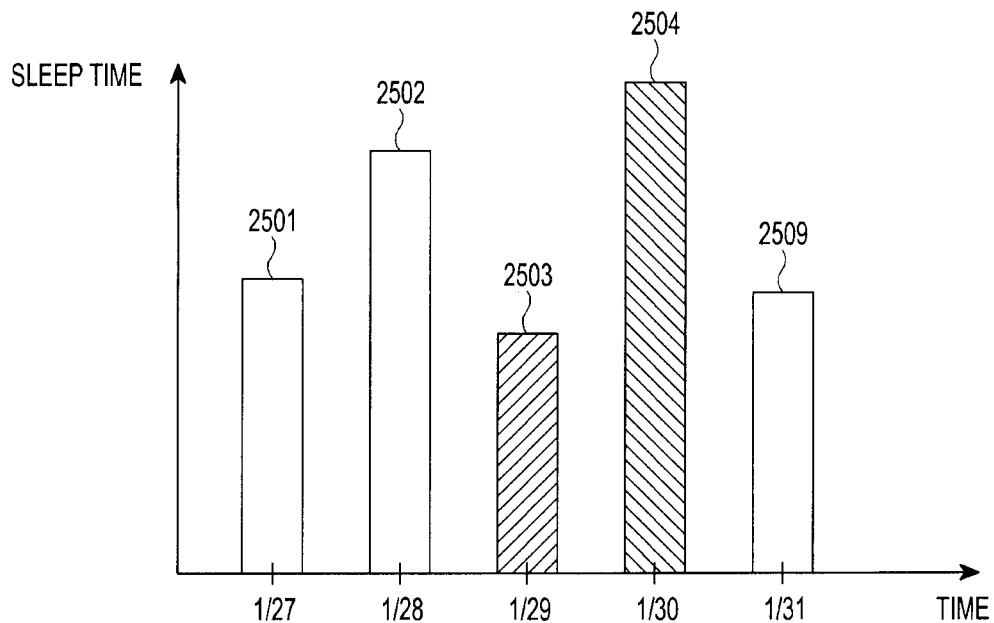
FIG. 25 is a sleeping graph, according to various embodiments of the present disclosure.

In operation 2410, the electronic device 101 may establish a sleep information database according to the received sleep information. In operation 2420, the electronic device 101 may analyze the sleep information. In operation 2430, the electronic device 101 may display an analysis result. For example, the electronic device 101 may display sleep information 2501 to 2505 for each date as illustrated in FIG. 25. The electronic device 101 may also display the sleep information 2503 corresponding to a date, at which a sleeping time is less than a predetermined first threshold value, and the sleep information 2504 corresponding to a date, at which a sleeping time is more than a predetermined second threshold value, with different colors from those of sleep information 2501, 2502, and 2505. In the meantime, the electronic device 101 may also further display sleep efficiency for each date.

FIGS. 26A to 26F are diagrams illustrating an example of screens of the electronic device according to various embodiments of the present disclosure.

Figure 26A:
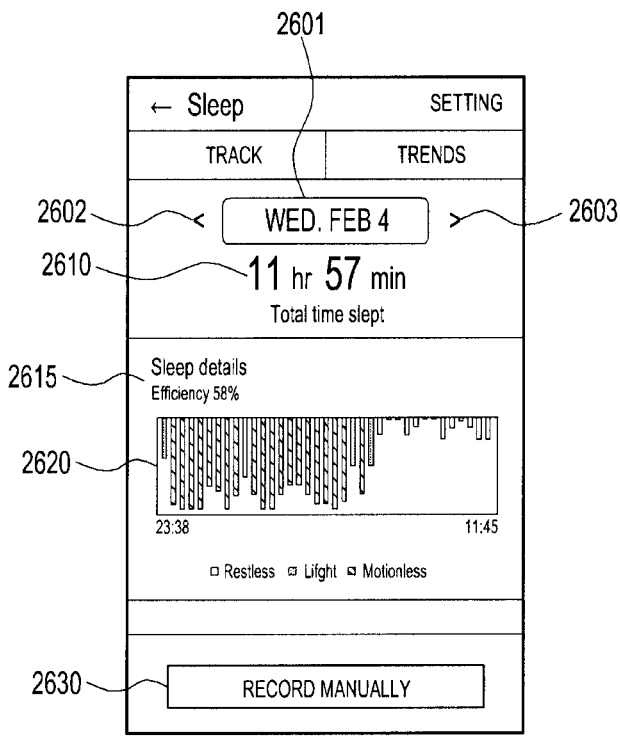
FIG. 26A is a diagram of an example of a user interface, according to various embodiments of the present disclosure.
Figure 26B:
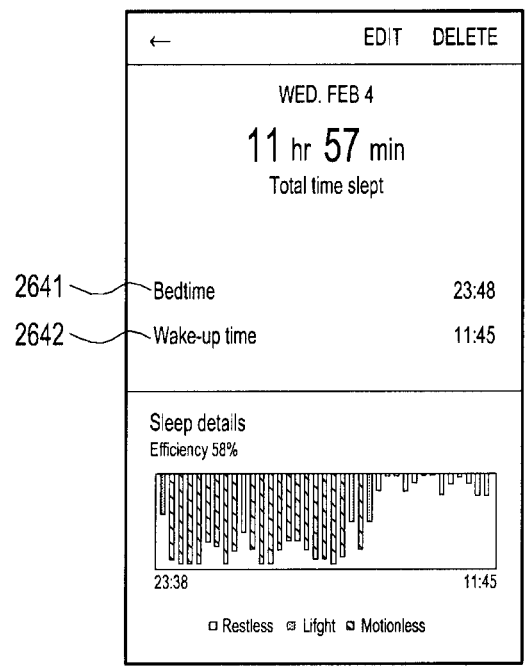
FIG. 26B is a diagram of an example of a user interface, according to various embodiments of the present disclosure.
Figure 26C:
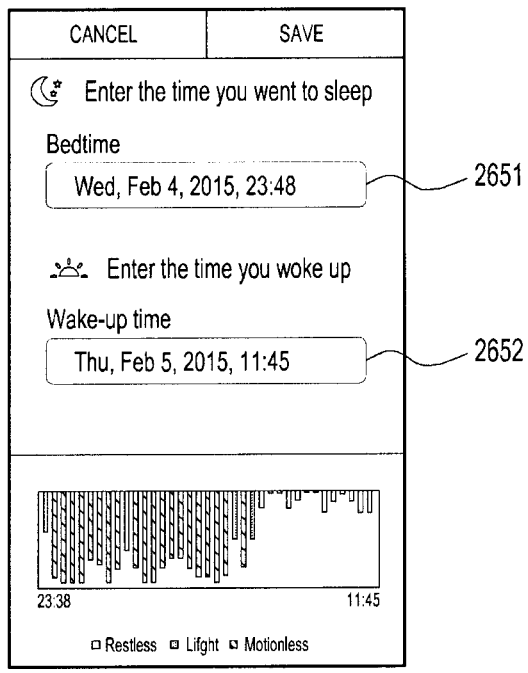
FIG. 26C is a diagram of an example of a user interface, according to various embodiments of the present disclosure.
Figure 26D:
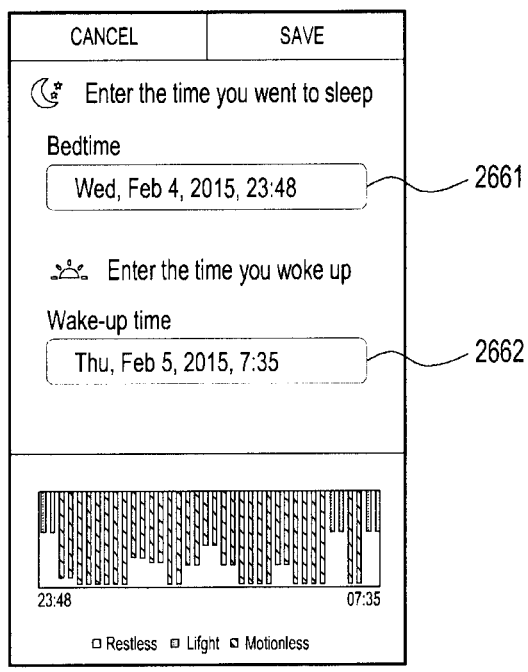
FIG. 26D is a diagram of an example of a user interface, according to various embodiments of the present disclosure.

Referring to FIG. 26A, the electronic device 101 may display a sleep information confirmation screen. The sleep information confirmation screen may include a target date 2601, target date change objects 2602 and 2603, a sleeping time 2610, sleep efficiency 2515, a sleeping graph 2620, and an edition object 2630. The electronic device 101 may determine and display sleep information for sleeping, and display the sleeping graph 2620 for at least one of a sleeping stage for each time and the sleep efficiency. In the meantime, when the edition object 2630 is activated, the electronic device 101 may display a sleep information input screen. The electronic device 101 may also display the sleep information input screen illustrated in FIG. 26C or 26D after entering the sleep information confirmation screen illustrated in FIG. 26B for a corresponding date including sleep information 2641 and 2642. FIG. 26C may be the sleep information input screen that provides pre-stored sleep information for a corresponding date as initial values 2651 and 2652, and FIGS. 26C and 26D may be the sleep information input screens which provide sleep information for reference determined based on the sleep pattern as sleep information 2661 and 2662 input from the initial values 2651 and 2652.

Figure 26E:
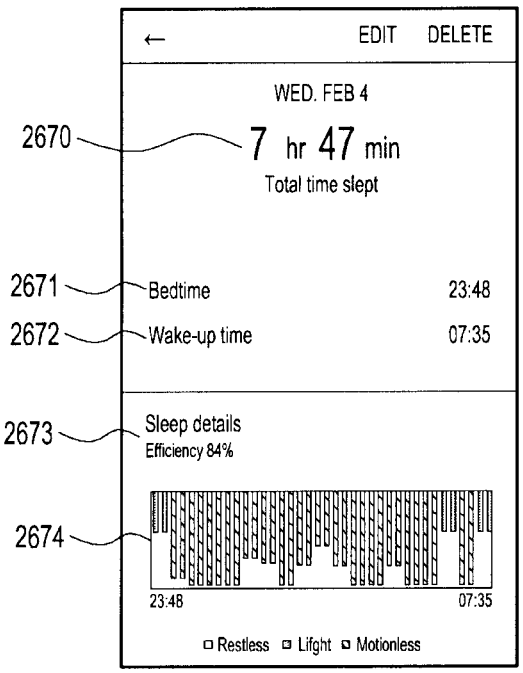
FIG. 26E is a diagram of an example of a user interface, according to various embodiments of the present disclosure.
Figure 26F:
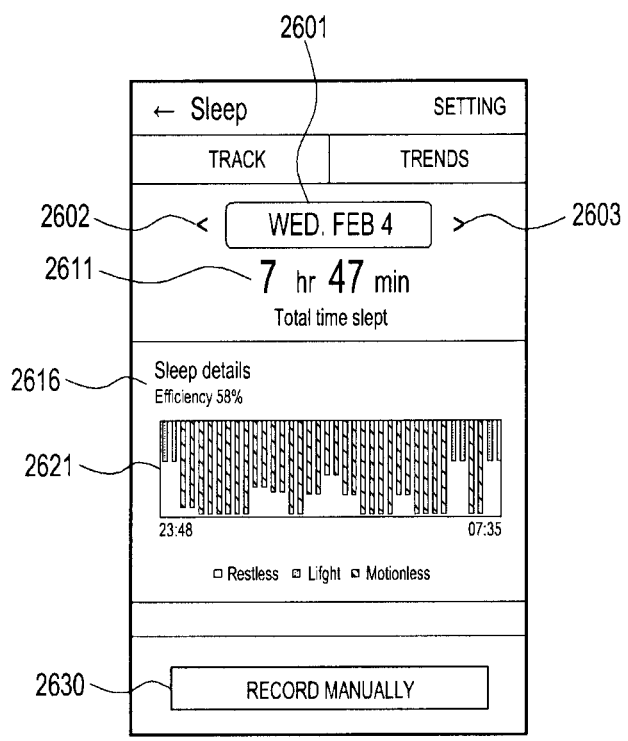
FIG. 26F is a diagram of an example of a user interface, according to various embodiments of the present disclosure.

FIG. 26E may illustrate an example of the sleep information confirmation screen of which an edition is completed. As illustrated in FIG. 26E, the electronic device 101 may display an edited sleeping time 2670, edited sleep information 2671 and 2672, edited sleep efficiency 2673, and an edited sleeping graph 2674 which are edited according to the edited sleep information. Further, as illustrated in FIG. 26F, the electronic device 101 may display an edited sleeping time 2611, edited sleep efficiency 2616, and an edited sleeping graph 2621 even on the sleep information confirmation screen. The electronic device 101 may automatically update the aforementioned edition process.

In various embodiments of the present disclosure, a method of controlling an electronic device may include: displaying a sleep information input screen determined according to a sleep pattern; obtaining sleep information corresponding to the sleep information input screen; and storing the obtained sleep information.

In various embodiments of the present disclosure, the sleep pattern includes a bedtime for reference and a wake-up time for reference, and the displaying of the sleep information input screen determined according to the sleep pattern may include displaying the sleep information input screen including the bedtime for reference and the wake-up time for reference.

In various embodiments of the present disclosure, the displaying of the sleep information input screen determined according to the sleep pattern may include displaying a bedtime input window and a wake-up time input window, setting and displaying the bedtime for reference as an initial value of the bedtime input window, and setting and displaying the wake-up time for reference as an initial value of the wake-up time input window.

In various embodiments of the present disclosure, the obtaining of the sleep information may include obtaining a time set in each of the bedtime input window and the wake-up time input window as the sleep information.

In various embodiments of the present disclosure, the method of controlling the electronic device may further include: obtaining data sensed from a sensor; and determining the sleep pattern based on the sensed data. The sensed data may contain at least one of a step count, movement information of the electronic device, skin hydration information, blood pressure information, Heart Rate (HR) information, Electroencephalogram (EEG) information, Electrocardiogram (ECG) information, Electromyograph (EMG) information, Electrooculogram (EOG) information, body temperature information, and noise information.

In various embodiments of the present disclosure, the method of controlling the electronic device may further include determining the sleep pattern based on pre-stored sleep information.

In various embodiments of the present disclosure, the determining of the sleep pattern based on the pre-stored sleep information may include determining the sleep pattern based on finally stored sleep information.

In various embodiments of the present disclosure, the determining of the sleep pattern based on the pre-stored sleep information may include determining the sleep pattern based on designated sleep information.

In various embodiments of the present disclosure, the determining of the sleep pattern based on the pre-stored sleep information may include determining the sleep pattern based on a weighted average for sleep information during a predetermined period.

In various embodiments of the present disclosure, the method of controlling the electronic device may further include determining an execution time of a sleep information management application, and the displaying of the sleep information input screen determined according to the sleep pattern may include determining the sleep pattern based on the sleep pattern and the execution time.

In various embodiments of the present disclosure, and the displaying of the sleep information input screen determined according to the sleep pattern may include: setting a section according to the sleep pattern, determining a first section, to which the execution time belongs; and displaying the sleep information input screen based on the first section and the sleep pattern.

In various embodiments of the present disclosure, the method of controlling the electronic device may further include determining an input target date of the sleep information according to the execution time.

In various embodiments of the present disclosure, the method of controlling the electronic device may further include determining the sleep pattern based on at least one of an obtainment time of an execution command for an application, a release time of an alarm application, information input into a schedule management application, a turn-on time of a display included in the electronic device, a turn-off time of the display, and an unlock time of the electronic device.

In various embodiments of the present disclosure, the method of controlling the electronic device may further include: receiving data from another electronic device; and determining the sleep pattern based on the data received from another electronic device.

In various embodiments of the present disclosure, the method of controlling the electronic device may further include: obtaining location information of the electronic device; and determining the sleep pattern based on the location information.

FIGS. 1-26F are provided as an example only. At least some of the operations discussed with respect to these figures can be performed concurrently, performed in different order, and/or altogether omitted. It will be understood that the provision of the examples described herein, as well as clauses phrased as "such as," "e.g.", "including", "in some aspects," "in some implementations," and the like should not be interpreted as limiting the claimed subject matter to the specific examples.

The above-described aspects of the present disclosure can be implemented in hardware, firmware or via the execution of software or computer code that can be stored in a recording medium such as a CD-ROM, a Digital Versatile Disc (DVD), a magnetic tape, a RAM, a floppy disk, a hard disk, or a magneto-optical disk or computer code downloaded over a network originally stored on a remote recording medium or a non-transitory machine-readable medium and to be stored on a local recording medium, so that the methods described herein can be rendered via such software that is stored on the recording medium using a general purpose computer, or a special processor or in programmable or dedicated hardware, such as an ASIC or FPGA. As would be understood in the art, the computer, the processor, microprocessor controller or the programmable hardware include memory components, e.g., RAM, ROM, Flash, etc. that may store or receive software or computer code that when accessed and executed by the computer, processor or hardware implement the processing methods described herein. In addition, it would be recognized that when a general purpose computer accesses code for implementing the processing shown herein, the execution of the code transforms the general purpose computer into a special purpose computer for executing the processing shown herein. Any of the functions and steps provided in the Figures may be implemented in hardware, software or a combination of both and may be performed in whole or in part within the programmed instructions of a computer. No claim element herein is to be construed under the provisions of 35 U.S.C. 112, sixth paragraph, unless the element is expressly recited using the phrase "means for".

Moreover, the embodiments disclosed in this specification are suggested for the description and understanding of technical content but do not limit the range of the present disclosure. Accordingly, the range of the present disclosure should be interpreted as including all modifications or various other embodiments based on the technical idea of the present disclosure.

What is claimed is:

1. A method comprising:
   acquiring a first time of a display of an electronic device being turned on and a second time of the display of the electronic device being turned off;
   identifying a first sleep pattern regarding a first period which is related to a first sleep of a user of the electronic device based on the first time and the second time;
   displaying, by the electronic device, a sleep information input screen providing at least one of a first wake-up time and a first bedtime identified according to the identified first sleep pattern, on the display of the electronic device;
   receiving a first input for adjusting the at least one of the first wake-up time and the first bedtime on the sleep information input screen;
   receiving a second input for storing the at least one of the adjusted first wake-up time and the adjusted first bed time;
   based on the received second input, storing a sleep information including at least one of the adjusted first wake-up time and the adjusted first bed time in a memory of the electronic device;
   identifying a second sleep pattern regarding a second period which is related to a second sleep of the user which is next to the first sleep of the user based on the stored sleep information;
   identifying a control command for causing the sleep information input screen to provide a information associated with the second period; and
   based on the identified control command, displaying the sleep information input screen providing at least one of a second wake-up time and a second bed time identified according to the identified second sleep pattern on the display of the electronic device.

2. The method of claim 1, further comprising:
   acquiring at least one sensing data by using at least one sensor of the electronic device, wherein the at least one sensing data includes at least one of an obtainment time of an execution command for an application, a release time of an alarm application, information input into a schedule management application, or an unlock time of the electronic device; and
   identifying the first sleep pattern regarding the first period based on the at least one sensing data, the first time, and the second time.

3. The method of claim 2, wherein the sleep information input screen includes a first input component for adjusting the first bedtime and a second input component for adjusting the first wake-up time.

4. The method of claim 1, further comprising:
   storing a first sleep information in the memory of the electronic device before the acquiring of the first time and the second time; and
   identifying the first sleep information,
   wherein identifying the first sleep pattern is further based on the first sleep information.

5. The method, of claim 1, further comprising:
   executing a sleep information management application,
   wherein identifying the first sleep pattern is further based on an execution time of the sleep information management application.

6. The method of claim 5, further comprising:
   identifying a section of the sleep information input screen based on the identified first sleep pattern; and
   adjusting the section based on the execution time.

7. A electronic device, comprising:
   a display;
   a memory; and
   at least one processor operatively coupled to the memory, configured to:
   acquire a first e of the display being turned on and a second time of the display being turned off,
   identify a first sleep pattern regarding a first period which is related to a first sleep of a user of the electronic device based on the first time and the second time,
   display, on the display, a sleep information input screen providing at least one of a first wake-up time and a first bedtime identified according to the identified sleep pattern;
   receive a first input for adjusting the at least one of the first wake-up time and the first bedtime on the sleep information input screen,
   receive a second input for storing the at least one of the adjusted first wake-up time and the adjusted first bed time,
   based on the received second input, store a sleep information including at least one of the adjusted first wake-up time and the adjusted first bed time in the memory,
   identify a second sleep pattern regarding a second period which is related to a second sleep of the user of the electronic device which is next to the first sleep of the user of the electronic device based on the stored sleep information,
   identify a control command for causing the sleep information input screen to provide a information associated with the second period, and
   based on the identified control command, display, on the display, the sleep information input screen providing at least one of a second wake-up time and a second bed time identified according to the identified second sleep pattern.

8. The electronic device of claim 7, further comprising:
   at least one sensor,
   wherein the at least one processor is further configured to:
   acquire at least one sensing data by using the at least one sensor, wherein the at least one sensing data includes at least one of an obtainment time of an execution command for an application, a release time of an alarm application, information input into a schedule management application, or an unlock time of the electronic device, and identify the first sleep pattern regarding the first period based on the at least one sensing data, the first time, and the second time.

9. The electronic device of claim 8, wherein the sleep information input screen includes a first input component for adjusting the first bedtime and a second input component for adjusting the first wake-up time.

10. The electronic device of claim 7, wherein the at least one processor is further configured to:
store a first sleep information in the memory before the acquiring of the first time and the second time; and
identify the first sleep information,
wherein identifying the first sleep pattern is further based on the first sleep information.

11. The electronic device of claim 7, wherein:
the at least one processor is further configured to:
execute a sleep information management application, and
identify the first sleep pattern based on an execution time of a sleep information management application.

12. The electronic device of claim 11, wherein:
the at least one processor is further configured to:
identify a section of the sleep information input screen based on the identified sleep pattern,
adjust the section based on the execution time.

13. A non-transitory computer-readable storage medium storing one or more processor-executable instructions, which when executed by at least one processor cause at least one processor to perform a method comprising the steps of:
acquiring a first time of a display of an electronic device being turned on and a second time of the display of the electronic device being turned off;
identifying a first sleep pattern regarding a first period which is related to a first sleep of a user of the electronic device based on the first time and the second time;
displaying, by the electronic device, a sleep information input screen providing at least one of a first wake-up time and a first bedtime identified according to the identified first sleep pattern on the display of the electronic device;
receiving a first input for adjusting the at least one of the first wake-up time and the first bedtime on the sleep information input screen;
receiving a second input for storing the at least one of the adjusted first wake-up time and the adjusted first bed time;
based on the received second input, storing a sleep information including at least one of the adjusted first wake-up time and the adjusted first bed time in a memory of the electronic device;
identifying a second sleep pattern regarding a second period which is related to a second sleep of the user of the electronic device which is next to the first sleep of the user of the electronic device based on the stored sleep information;
identifying a control command for causing the sleep information input screen to provide a information associated with the second period; and
based on the identified control command, displaying the sleep information input screen providing at least one of a second wake-up time and a second bed time identified according to the identified second sleep pattern on the display of the electronic device.

* * * * *